(12) United States Patent
McGonigle et al.

(10) Patent No.: US 6,168,954 B1
(45) Date of Patent: Jan. 2, 2001

(54) SOYBEAN GLUTATHIONE-S-TRANSFERASE ENZYMES

(75) Inventors: Brian McGonigle, Wilmington, DE (US); Daniel P. O'Keefe, Ridley Park, PA (US)

(73) Assignee: E. I. du Pont de Nemours & Company, Wilmington, DE (US)

( * ) Notice: Under 35 U.S.C. 154(b), the term of this patent shall be extended for 0 days.

(21) Appl. No.: 09/247,373

(22) Filed: Feb. 10, 1999

Related U.S. Application Data

(63) Continuation-in-part of application No. 08/924,747, filed on Sep. 5, 1997.

(51) Int. Cl.$^7$ .................................................. C12N 15/82
(52) U.S. Cl. .................. 435/468; 435/471; 435/410; 435/252.3; 435/6; 435/15; 536/23.2
(58) Field of Search ..................... 536/23.2; 435/410, 435/252.3, 468, 471, 6, 15

(56) References Cited

U.S. PATENT DOCUMENTS

| | | | |
|---|---|---|---|
| 5,073,677 | 12/1991 | Helmer et al. | 800/205 |
| 5,589,614 | 12/1996 | Bridges et al. | 800/205 |

FOREIGN PATENT DOCUMENTS

| | | | |
|---|---|---|---|
| 0 256 223 | 5/1987 | (EP) . | |
| 0 330 479 | 8/1989 | (EP) . | |
| WO 93 01294 | 1/1993 | (WO) . | |
| WO 96/23072 | 8/1996 | (WO) . | |
| WO 97/11189 | 3/1997 | (WO) . | |
| WO99/14337 | 9/1999 | (WO) | C12N/15/54 |

OTHER PUBLICATIONS

McGonigle et al. Plant Physiology (1998) 117: 332, 1998.*
Andrews, Nucleotide sequence of a Glutathione transferase from soybean with activity towards herbicides, *EMBL Sequence Data Library*, XP002113992.
Skipsey, et al., Substrate and thiol specificity of a stress–inducible glutathione transferase from soybean, *FEBS Letters*, 409, pp. 370–374, 1997.
McGonigle et al., Untitled, *EMBL Sequence Data Library*, XP002113990, Jun. 1, 1998.
Ulmasov et al., The Soybean GH2/4 Gene that encodes a glutathione S–Transferase has a promoter that is activated by a wide range of chemical agents, Plant Physiology, vol. 108, No. 3, Jul. 1, 1995 pp. 919–927.
Timmerman, Molecular Characterization of Corn Glutathione S–Transferase Isozymes Involved in Herbicide Detoxication, Physiologia Plantarum, vol. 77, No. SYMP. Jan. 1, 1989 pp. 465–471 XP002000778.
McGonigle et al., Pesticide Biochemistry and Physiology 62, 15–25, Homoglutathione Selectivity by Soybean Glutathione S–Transferases, 1998.
David C. Holt et al., Characterization of the Safener–Induced Glutathione S–Transferase Isoform II from Maize, *Planta*, 196, 295–302, 1995.
F. Droog, Plant Glutathione S–Transferases, a Tale of Theta and Tau, *J. Plant Growth Regul*, 16, 95–107, 1997.
Laura Rossini et al., Characterization of Glutathione S–Transferase Isoforms in Three Maise Inbred Lines Exhibiting Differential Sensitivity of Alachlor, *Plant Physiol*, 112, 1595–1600, 1996.
van der Zaal et al., *Plant Mol. Biol.*, 16(6), 983–998, 1991.
Kathleen A. Marrs, The Functions and Regulation of Glutathione S–Transferases in Plants, *Annu. Rev. Plant Physiol. Plant Mol. Biol.*, 47, 127–158, 1996.
Sharad S. Singhal et al., Purification and Characterization of Glutathione S–Transferase from Sugarcane Leaves, *Phytochemistry*, 30, No. 5, 1409–1414, 1991.
Robert Edwards et al., Glutathione Transferases in Wheat (Triticum) Species with Activity toward Fenoxaprop–Ethyl and Other Herbicides, *Pesticide Biochemistry and Physiology*, 54, 94–104, 1996.
Czarnecka et al., *Mol. Cell. Biol.*, 8(3), 1113–1122, 1988.
Michael A. Wosnick et al., Total Chemical Synthesis and Expression in *Escherichia coli* of a Maize Gluthathione–Transferase (GST) Gene, *Gene*, 76, 153–160, 1989.
Ian Jepson et al., Cloning and Characterization of Maize Herbicide Safener–induced cDNAs Encoding Subunits of Glutathione S–Transferase Isoforms, I, II, and IV, *Plant Molecular Biology*, 26, 1855–1866, 1994.
Dianne A.M. van der Kop et al., Isolation and Characterization of an Auxin–Inducible Glutathione S–Transferase Gene of ARabidopsis Thaliana, *Plant Molecular Biology*, 30, 839–844, 1996.
Blattner et al., *Science*, 277(5331), 1453–1474, 1997.
Dilip M. Shah et al., Structural Analysis of a Maize Gene Coding for Glutathione–S–Transferase Involved in Herbicide Detoxification, *Plant Molecular Biology*,6, 203–211, 1986.
Robert E. Moore et al., Cloning and Expression of a cDNA Encoding a Maize Glutathione–S–Transferase in *E. Coli*, *Nucleic Acids Research*, 14, No. 18, 7227–7235, 1986.

(List continued on next page.)

*Primary Examiner*—Ponnathapu Achutamurthy
*Assistant Examiner*—Kathleen Kerr

(57) ABSTRACT

This invention relates to isolated nucleic acid fragments encoding all or a substantial portion of soybean glutathione-S-transferase (GST) enzymes involved in the detoxification of xenobiotic compounds in plants and seeds. The invention also relates to the construction of chimeric genes encoding all or a substantial portion of soybean GST enzymes, host cells transformed with those genes and methods for the recombinant production of soybean GST enzymes. Methods of constructing transgenic plants having altered levels of GST enzymes and screens for identifying soybean GST enzyme substrates and soybean GST enzyme inhibitors are also provided.

15 Claims, No Drawings

OTHER PUBLICATIONS

Kriton K. Hatzios et al., Herbicide Safeners, *J. Environ. Sci. Health*, B31(3), 545–553, 1996.

Thomas Flury et al., A 2,4–D–Inducible Glutathione S–Transferase from Soybean (Glycine Max)., *Physiologia Plantarum*, 94, 312–318, 1995.

Robert Edwards, Characterization of Glutathione Transferases and Glutathione Peroxidases in Pea, *Physiologia Plantarum*, 98, 594–604, 1996.

McGonigle, Brian et al., Role of glutathione conjugation in the detoxification of sulfonylurea herbicides in plants, Book of Abstracts, 216th American Chemical Society, (1998), (Abstract).

* cited by examiner

SEQUENCE LISTING

<160> NUMBER OF SEQ ID NOS: 56

<210> SEQ ID NO 1
<211> LENGTH: 886
<212> TYPE: DNA
<213> ORGANISM: SOYBEAN

<400> SEQUENCE: 1
caaacactac acgtgccatg atctgtctcc atgagaaaga ggtcgatttt gaacttgttc      60
cggtcaatgt gttcgctgct gagcacaagc agcctccttt tctctccaag aatccctttg     120

-continued

```
gtttcattcc agtactggaa gatggtgatc tcactctttt tgagtccagg gccattaccg    180
catacgtggc tgaaaaattc aaggaaacag aacccgatct gataaggcac aaggatgcaa    240
aagaagcagc actggtgaag gtatggacag aggtagagtc tcattactac gagccagcag    300
tgtcgcccat tatctacgag tacttcgtgg cccctttcca aggcaaagaa cccgacaagt    360
cagtgattga caccaacgtt gagaagctga agacggtgct tgatgtgtac gaggccaagc    420
tgagcagcac caagtacctt gctggggact tttatagcct tgctgatctt agccatgttt    480
ctgaaactca ctacttgatg cagacccctt gtgcttccat gatcaatgag cttcctcatg    540
taaaggcttg gtgggaggat atctcttcta ggcctgcttt caataaggtt gtgggaggaa    600
tgagttttgg tcagaatcat tgaggaatga gtgtgttttg tgaggttcaa ttactaccta    660
atttgttgca gtatctagtc aagcaaatgt ggtgttgggt gttcttgaaa cttgtttcat    720
ttcttataac tagaattaat taggaaaacg aatcaatttt tagagggtc tttaagaaaa    780 aggactttaa tagttccttt tgtcttattt gattaattta aaattttatg ttgtagtgtt    840
ttgatgatat gtttaatat cctatttcaa aaaaaaaaaa aaaaaa              886
```

<210> SEQ ID NO 2
<211> LENGTH: 201
<212> TYPE: PRT
<213> ORGANISM: SOYBEAN

<400> SEQUENCE: 2

```
Met Ile Cys Leu His Glu Lys Glu Val Asp Phe Glu Leu Val Pro Val
  1               5                  10                  15

Asn Val Phe Ala Ala Glu His Lys Gln Pro Pro Phe Leu Ser Lys Asn
             20                  25                  30

Pro Phe Gly Phe Ile Pro Val Leu Glu Asp Gly Asp Leu Thr Leu Phe
         35                  40                  45

Glu Ser Arg Ala Ile Thr Ala Tyr Val Ala Glu Lys Phe Lys Glu Thr
     50                  55                  60

Glu Pro Asp Leu Ile Arg His Lys Asp Ala Lys Glu Ala Ala Leu Val
 65                  70                  75                  80

Lys Val Trp Thr Glu Val Glu Ser His Tyr Tyr Glu Pro Ala Val Ser
                 85                  90                  95

Pro Ile Ile Tyr Glu Tyr Phe Val Ala Pro Phe Gln Gly Lys Glu Pro
            100                 105                 110

Asp Lys Ser Val Ile Asp Thr Asn Val Glu Lys Leu Lys Thr Val Leu
        115                 120                 125

Asp Val Tyr Glu Ala Lys Leu Ser Ser Thr Lys Tyr Leu Ala Gly Asp
    130                 135                 140

Phe Tyr Ser Leu Ala Asp Leu Ser His Val Ser Glu Thr His Tyr Leu
145                 150                 155                 160

Met Gln Thr Pro Cys Ala Ser Met Ile Asn Glu Leu Pro His Val Lys
                165                 170                 175

Ala Trp Trp Glu Asp Ile Ser Ser Arg Pro Ala Phe Asn Lys Val Val
            180                 185                 190

Gly Gly Met Ser Phe Gly Gln Asn His
        195                 200
```

<210> SEQ ID NO 3
<211> LENGTH: 1007
<212> TYPE: DNA
<213> ORGANISM: SOYBEAN

-continued

<400> SEQUENCE: 3

```
cacgacactg agcatcagca atggcaagcg caagtgttgg taaagaactg acgctgtatt    60
cgtattggag gagctcttgt tcccaccgag tccgaatcgc tctcaacctc aaagggctta   120
aatacgaata caagcccgtc aatctgctca agggagaaca atctcgccct gagtttctcc   180
agctcaatcc tgttggttgt gtccccgttc tagtggatga ccacgttgtt ctctatgact   240
ctttcgccat tattatgtat ttggaagata agtatcctca caatcctttg ctccctcatg   300
atatttacaa gagagcaatc aatttccagg ctgctagtgt tgtttcctca acaatacaac   360
ctcttcataa cttgagttta ctgaactaca ttggggagaa agttggccct gatgaaaaac   420
ttccttgggc ccaaagtata attagaagag gctttaaagc actggaaaag ctattgaaag   480
accacacagg aagatatgca actggagatg aagttttcct ggcagatata tttttagcac   540
ctcagttaca tgcagcattt aagagattca acattcacat gaacgagttc cctattctag   600
caagattgca tgagacatat aatgagatcc ctgcattcca ggaggctctg ccagagaacc   660
agcctgatgc agtacactag ttgaaccaat aatttgggac agaaatatga gttgatatta   720
agttggagaa attgcagcag gagctactta ttcagcatcc ggatgaattc gttgttaaag   780
tattaaaata tgatactcaa tatagcaata aggttgccac atgcaatatt tattgcacac   840
atcatgtaca attgaaaaaa aaaaattggt ttcgggtgta tgtctataaa gccttatgtt   900
tattttccat tcatattct tcccagaatc ccagtcaatg tagcttgatg gatgattctt   960
aatggtgttt atggttgaat tggtgtttca aaaaaaaaaa aaaaaaa                1007
```

<210> SEQ ID NO 4
<211> LENGTH: 219
<212> TYPE: PRT
<213> ORGANISM: SOYBEAN

<400> SEQUENCE: 4

```
Met Ala Ser Ala Ser Val Gly Lys Glu Leu Thr Leu Tyr Ser Tyr Trp
  1               5                  10                  15

Arg Ser Ser Cys Ser His Arg Val Arg Ile Ala Leu Asn Leu Lys Gly
                 20                  25                  30

Leu Lys Tyr Glu Tyr Lys Pro Val Asn Leu Leu Lys Gly Glu Gln Ser
             35                  40                  45

Arg Pro Glu Phe Leu Gln Leu Asn Pro Val Gly Cys Val Pro Val Leu
         50                  55                  60

Val Asp Asp His Val Val Leu Tyr Asp Ser Phe Ala Ile Ile Met Tyr
 65                  70                  75                  80

Leu Glu Asp Lys Tyr Pro His Asn Pro Leu Leu Pro His Asp Ile Tyr
                 85                  90                  95

Lys Arg Ala Ile Asn Phe Gln Ala Ala Ser Val Val Ser Ser Thr Ile
            100                 105                 110

Gln Pro Leu His Asn Leu Ser Leu Leu Asn Tyr Ile Gly Glu Lys Val
        115                 120                 125

Gly Pro Asp Glu Lys Leu Pro Trp Ala Gln Ser Ile Ile Arg Arg Gly
    130                 135                 140

Phe Lys Ala Leu Glu Lys Leu Leu Lys Asp His Thr Gly Arg Tyr Ala
145                 150                 155                 160

Thr Gly Asp Glu Val Phe Leu Ala Asp Ile Phe Leu Ala Pro Gln Leu
                165                 170                 175

His Ala Ala Phe Lys Arg Phe Asn Ile His Met Asn Glu Phe Pro Ile
            180                 185                 190
```

```
Leu Ala Arg Leu His Glu Thr Tyr Asn Glu Ile Pro Ala Phe Gln Glu
        195                 200                 205

Ala Leu Pro Glu Asn Gln Pro Asp Ala Val His
        210                 215

<210> SEQ ID NO 5
<211> LENGTH: 902
<212> TYPE: DNA
<213> ORGANISM: SOYBEAN

<400> SEQUENCE: 5
ggcttgacga ggaagtgtta ttagagttct ggccaagtcc atttgggatg agggtcagga     60
ttgcacttgc tgaaaagggt atcaaatatg agtacaaaga agaggacttg aggaacaaga    120
gtcctcttct cctccaaatg aacccggttc acaagaagat tccggttctc atccacaatg    180
gcaaacccat ttgtgaatcc ctcattgctg ttcagtacat tgaggaggtt tggaatgaca    240
gaaatccctt gttgccttct gacccttacc agagagctca gactagattc tgggctgatt    300
atgttgataa agagatatat gatcttggaa ggaagatttg gacatcaaaa ggagaagaaa    360
aagaagctgc caagaaggag ttcatagaag cccttaaatt gttggaggaa cagctgggag    420
acaagactta ttttggagga gacaatctag gttttgtgga tatagcgctt gttccattct    480
acacttggtt caaagcctat gagacttttg cacccctcaa catagagagt gagtgcccca    540
agtttattgc ttgggccaag aggtgccttc agaaagaaag cgttgccaag tctcttcctg    600
atcagcaaaa ggtttatgag ttcattatgg atctaagaaa gaagttaggc attgagtagg    660
ttggagctta atggccattg tgaagtagtg gttttccatt ggtcgttctt agcctttcaa    720
ataagtaata tttgtgtaat aaaaggcact tagatgtgcc aaacttcgtg ctttctgtag    780
gaatgtgtgg gttttggaaa atctctgatg tatctttcat gtgtttgttg gttttgtaat    840
tttttttttgg tattgtctta tacttgaata atttgagact aaaaaaaaaa aaaaaaaaa    900
aa                                                                   902

<210> SEQ ID NO 6
<211> LENGTH: 218
<212> TYPE: PRT
<213> ORGANISM: SOYBEAN

<400> SEQUENCE: 6

Met Ser Asp Glu Val Val Leu Leu Asp Phe Trp Pro Ser Pro Phe Gly
  1               5                  10                  15

Met Arg Val Arg Ile Ala Leu Ala Glu Lys Gly Ile Lys Tyr Glu Tyr
             20                  25                  30

Lys Glu Glu Asp Leu Arg Asn Lys Ser Pro Leu Leu Leu Gln Met Asn
         35                  40                  45

Pro Val His Lys Lys Ile Pro Val Leu Ile His Asn Gly Lys Pro Ile
     50                  55                  60

Cys Glu Ser Leu Ile Ala Val Gln Tyr Ile Glu Glu Val Trp Asn Asp
 65                  70                  75                  80

Arg Asn Pro Leu Leu Pro Ser Asp Pro Tyr Gln Arg Ala Gln Thr Arg
                 85                  90                  95

Phe Trp Ala Asp Tyr Val Asp Lys Lys Ile Tyr Asp Leu Gly Arg Lys
            100                 105                 110

Ile Trp Thr Ser Lys Gly Glu Glu Lys Glu Ala Ala Lys Lys Glu Phe
        115                 120                 125
```

```
Ile Glu Ala Leu Lys Leu Leu Glu Glu Gln Leu Gly Asp Lys Thr Tyr
         130                 135                 140
Phe Gly Gly Asp Asn Leu Gly Phe Val Asp Ile Ala Leu Val Pro Phe
145                 150                 155                 160
Tyr Thr Trp Phe Lys Ala Tyr Glu Thr Phe Gly Thr Leu Asn Ile Glu
                 165                 170                 175
Glu Cys Pro Lys Phe Ile Ala Trp Ala Lys Arg Cys Leu Gln Lys Glu
             180                 185                 190
Ser Val Ala Lys Ser Leu Pro Asp Gln Gln Lys Val Tyr Glu Phe Ile
         195                 200                 205
Met Asp Leu Arg Lys Lys Leu Gly Ile Glu
     210                 215

<210> SEQ ID NO 7
<211> LENGTH: 895
<212> TYPE: DNA
<213> ORGANISM: SOYBEAN

<400> SEQUENCE: 7
cacaactttg cccccttgta aaacttctta ttgtgatgtc taaaagcgaa gacttgaagc      60
ttttgggagg ctggttcagc ccatttgccc tgagggtgca gattgcccct aacctcaagg     120
gtctagaata tgaggttgtt gaagagacct tgaatcccaa aagtgacctg cttcttaagt     180
ccaaccctgt gcacaagaaa atcccagttt tcttccatgg agataaagtc atttgtgaat     240
ctgcaatcat agttgagtac attgatgagg cttggactaa tgttccctcc atccttccac     300
aaaatgctta tgatcgtgct aatgctcgat tttggttttgc ctacattgat gagaagtggt     360
ttacgtcctt gagaagtgtt ctagtggctg aagatgatga ggcaaagaag ccacactttg     420
agcaagcaga agaagggctt gagaggttgg aagaagtgtt caacaagtac agtgaaggga     480
aggcctattt cggaggagat agcattggat tcattgacat tggttttggg agcttcttga     540
gttggatgag agtcatagag gagatgagtg aagaaaaatt gcttgatgaa aagaagcacc     600
ctggtttgac ccaatgggct gaaacgtttg ctgctgatcc tgctgtgaag ggcattcttc     660
cagagactga taagcttgtt gagtttgcca agattcttca gctaaaatgg actgctgcag     720
cagctgcagc tgcaaagtaa atggaatcaa attaattgcg agagtatttt caaaattgtt     780
gtccaagttg tttttatctc aggctatgtt gttgcaactt tatttattta aaagttattt     840
taaatttaaa atgtaaaata ttaagaaagt ttaagtaagt tagttgaaaa atttt          895

<210> SEQ ID NO 8
<211> LENGTH: 234
<212> TYPE: PRT
<213> ORGANISM: SOYBEAN

<400> SEQUENCE: 8

Met Ser Lys Ser Glu Asp Leu Lys Leu Leu Gly Gly Trp Phe Ser Pro
  1               5                  10                  15
Phe Ala Leu Arg Val Gln Ile Ala Leu Asn Leu Lys Gly Leu Glu Tyr
                 20                  25                  30
Glu Val Val Glu Glu Thr Leu Asn Pro Lys Ser Asp Leu Leu Leu Lys
             35                  40                  45
Ser Asn Pro Val His Lys Lys Ile Pro Val Phe Phe His Gly Asp Lys
         50                  55                  60
Val Ile Cys Glu Ser Ala Ile Ile Val Glu Tyr Ile Asp Glu Ala Trp
 65                  70                  75                  80
```

```
Thr Asn Val Pro Ser Ile Leu Pro Gln Asn Ala Tyr Asp Arg Ala Asn
                85                  90                  95

Ala Arg Phe Trp Phe Ala Tyr Ile Asp Glu Lys Trp Phe Thr Ser Leu
            100                 105                 110

Arg Ser Val Leu Val Ala Glu Asp Glu Ala Lys Lys Pro His Phe
            115                 120                 125

Glu Gln Ala Glu Glu Gly Leu Glu Arg Leu Glu Val Phe Asn Lys
    130                 135                 140

Tyr Ser Glu Gly Lys Ala Tyr Phe Gly Gly Asp Ser Ile Gly Phe Ile
145                 150                 155                 160

Asp Ile Gly Phe Gly Ser Phe Leu Ser Trp Met Arg Val Ile Glu Glu
                165                 170                 175

Met Ser Gly Arg Lys Leu Leu Asp Glu Lys Lys His Pro Gly Leu Thr
            180                 185                 190

Gln Trp Ala Glu Thr Phe Ala Ala Asp Pro Ala Val Lys Gly Ile Leu
            195                 200                 205

Pro Glu Thr Asp Lys Leu Val Glu Phe Ala Lys Ile Leu Gln Leu Lys
    210                 215                 220

Trp Thr Ala Ala Ala Ala Ala Ala Lys
225                 230
```

<210> SEQ ID NO 9
<211> LENGTH: 931
<212> TYPE: DNA
<213> ORGANISM: SOYBEAN

<400> SEQUENCE: 9

```
ctgcaggtag ttttctgtt tgaagtgcta caaacaatgg cagctactca ggaagatgtg    60
acgcttttgg gagttgttgg aagcccgttt gtgtgcaggg tccagattgc cctcaaattg   120
aagggaattg aatgcaaatt tttggaagaa aatttggcaa acaagagtga tctacttctc   180
aaatccaacc ccgtttacaa gaaggttcca gtgtttattc ataatgagaa gcccatagca   240
gagtctcttg tgattgttga gtacattgat gagacatgga agaacaaccc catcttgcct   300
tctgatcctt accaaagatc ctttgctcgg ttttggtcca agttcataga tgacaagatt   360
gtgggtgctt catggaaatc tgttttcacg gttgatgaga agagcgtga gaagaatgtt   420
gaagaatcgt tggaggctct gcagtttctt gagaatgaac tacaggacaa aggttctttt   480
ggaggagatg aatttggatt tgtagatatt gctggtgtct tcattgcatt ttcaatccca   540
attttccaag aagtagcagg gttgcaatta ttcaccagtg agaaatttcc taagctcttc   600
aaatggagcc aagagttgat caaccaccct gttgtcaaag atgtccttcc tcctagagaa   660
ccactttttg ccttcttcaa atccctctat gaaagccttt ctgcttcaaa atagattgtt   720
taagaatgat tgtgtgaact acttgtcgct cattgaatta ttgttgtttg aatttcatgt   780
caatttgata ctatatgtaa tttagtaacc tgggatatta ggatatcccc aaggaacaaa   840
gaatcctagg atttttgttc cattttggcc atttcagtta ataattaaag aaactctatt   900
tttcttgtt acaaaaaaaa aaaaaaaaa a                                    931
```

<210> SEQ ID NO 10
<211> LENGTH: 225
<212> TYPE: PRT
<213> ORGANISM: SOYBEAN

-continued

```
<400> SEQUENCE: 10

Met Ala Ala Thr Gln Glu Asp Val Thr Leu Leu Gly Val Val Gly Ser
  1               5                  10                  15

Pro Phe Val Cys Arg Val Gln Ile Ala Leu Lys Leu Lys Gly Ile Glu
             20                  25                  30

Cys Lys Phe Leu Glu Glu Asn Leu Ala Asn Lys Ser Asp Leu Leu Leu
         35                  40                  45

Lys Ser Asn Pro Val Tyr Lys Val Pro Val Phe Ile His Asn Glu
     50                  55                  60

Lys Pro Ile Ala Glu Ser Leu Val Ile Val Glu Tyr Ile Asp Glu Thr
 65                  70                  75                  80

Trp Lys Asn Asn Pro Ile Leu Pro Ser Asp Pro Tyr Gln Arg Ser Phe
                 85                  90                  95

Ala Arg Phe Trp Ser Lys Phe Ile Asp Asp Lys Ile Val Gly Ala Ser
            100                 105                 110

Trp Lys Ser Val Phe Thr Val Asp Glu Lys Glu Arg Glu Lys Asn Val
        115                 120                 125

Glu Glu Ser Leu Glu Ala Leu Gln Phe Leu Glu Asn Glu Leu Gln Asp
130                 135                 140

Lys Arg Phe Phe Gly Gly Asp Glu Phe Gly Phe Val Asp Ile Ala Gly
145                 150                 155                 160

Val Phe Ile Ala Phe Ser Ile Pro Ile Phe Gln Glu Val Ala Gly Leu
                165                 170                 175

Gln Leu Phe Thr Ser Glu Lys Phe Pro Lys Leu Phe Lys Trp Ser Gln
            180                 185                 190

Glu Leu Ile Asn His Pro Val Val Lys Asp Val Leu Pro Pro Arg Glu
        195                 200                 205

Pro Leu Phe Ala Phe Phe Lys Ser Leu Tyr Glu Ser Leu Ser Ala Ser
    210                 215                 220

Lys
225

<210> SEQ ID NO 11
<211> LENGTH: 946
<212> TYPE: DNA
<213> ORGANISM: SOYBEAN

<400> SEQUENCE: 11
ttgcactaca aatcagtttt ctacttgaat cttcgttatc cttcttttt tctccttgaa      60 ctcgaatatt cactatggca gatgaggtgg ttctgctaga tttctggcca agtccatttg    120
ggatgagggt caggattgca cttgctgaaa agggtatcaa atatgagtcc aaagaagagg    180
acttgcagaa caagagccct tgctcctca aaatgaaccc ggttcacaag aaaatcccgg     240
ttctcatcca caatggcaaa cccatttgtg aatctctcgt tgctgttcag tacattgagg    300
aggtctggaa tgacagaaat cccttgttgc cttctgaccc ttaccagaga gctcaggcta    360
gattctgggc tgactttgtt gacaataaga tatttgatct tggaagaaag atttggacat    420
caaagggaga agaaaaagaa gctgccaaaa aggagttcat agaggccctt aaattattgg    480
aggaacagct gggagacaag acttattttg gaggagacga tctaggtttt gtggatatag    540
cacttattcc attcgacact tggttcaaga cttttggcag cctcaacata gagagtgagt    600
gccccaagtt tgttgcttgg gccaagaggt gcctgcagaa agacagtgtt gccaagtctc    660
ttcctgatca acacaaggtc tatgagttca ttatggacat aagaaagaag ttcgacattg    720
```

-continued agtaggttca tgttggattt taatagccat agtgacgtat tgatcattct tggcctttca    780
actaaatagt atttgtgtag taaattaaag gcacttggat gtaccaaact tcatgctttt    840
tgtaggagtg cgtaggtttt aaaaattttc tgatgtatct ttcatgtgtt tgttggtttt    900
gtaacagaat atttcctata ttatacataa aaaaaaaaaa aaaaaa                  946

<210> SEQ ID NO 12
<211> LENGTH: 216
<212> TYPE: PRT
<213> ORGANISM: SOYBEAN

<400> SEQUENCE: 12

Met Ala Asp Glu Val Val Leu Leu Asp Phe Trp Pro Ser Pro Phe Gly
 1               5                  10                  15

Met Arg Val Arg Ile Ala Leu Ala Glu Lys Gly Ile Lys Tyr Glu Ser
             20                  25                  30

Lys Glu Glu Asp Leu Gln Asn Lys Ser Pro Leu Leu Leu Lys Met Asn
         35                  40                  45

Pro Val His Lys Lys Ile Pro Val Leu Ile His Asn Gly Lys Pro Ile
     50                  55                  60

Cys Glu Ser Leu Val Ala Val Gln Tyr Ile Glu Glu Val Trp Asn Asp
 65                  70                  75                  80

Arg Asn Pro Leu Leu Pro Ser Asp Pro Tyr Gln Arg Ala Gln Ala Arg
                 85                  90                  95

Phe Trp Ala Asp Phe Val Asp Asn Lys Ile Phe Asp Leu Gly Arg Lys
            100                 105                 110

Ile Trp Thr Ser Lys Gly Glu Glu Lys Glu Ala Ala Lys Lys Glu Phe
        115                 120                 125

Ile Glu Ala Leu Lys Leu Leu Glu Glu Gln Leu Gly Asp Lys Thr Tyr
    130                 135                 140

Phe Gly Gly Asp Asp Leu Gly Phe Val Asp Ile Ala Leu Ile Pro Phe
145                 150                 155                 160

Asp Thr Trp Phe Lys Thr Phe Gly Ser Leu Asn Ile Glu Ser Glu Cys
                165                 170                 175

Pro Lys Phe Val Ala Trp Ala Lys Arg Cys Leu Gln Lys Asp Ser Val
            180                 185                 190

Ala Lys Ser Leu Pro Asp Gln His Lys Val Tyr Glu Phe Ile Met Asp
        195                 200                 205

Ile Arg Lys Lys Phe Asp Ile Glu
    210                 215

<210> SEQ ID NO 13
<211> LENGTH: 977
<212> TYPE: DNA
<213> ORGANISM: SOYBEAN

<400> SEQUENCE: 13
ctgattcccg gctcaataag aggagaatac cttaggaatc cataagaaac attaattcac     60
cactatagtt gttctgttag aagtgctaca acaacaatg gctgctaatc aggaagatgt    120
gaagcttttg ggagctactg gaagcccatt tgtgtgcagg gttcagattg ccctcaagtt    180
gaagggagtt caatacaaat ttttggaaga aaatttgagg aacaagagtg aactgcttct    240
caaatccaac ccagttcaca gaaggttcc agtgttattt cacaatgaga agcccatagc    300
agagtctctt gtgattgttg aatacattga tgagacatga agaacaacc ccatcttgcc    360 ttctgatcct taccaaagag ccttggctcg tttctggtcc aaattcattg atgacaaggt    420

-continued

```
tgtgggtgct gcatggaaat atatttatac tgttgatgag aaagagcgtg agaagaatgt      480
tgaagagtca tatgaggctc tgcagtttct tgagaatgag ctgaaggaca agaagttttt      540
tggaggagag gaaattgggt tggtagatat tgctgctgtc ttcatagcat tttggatccc      600
tataattcaa gaagtattgg gtttgaagtt attcacaagt gagaaatttc ctaagctcta      660
caaatggagc caagagttca tcaaccaccc tgttgtcaaa caagtccttc ctcctagaga      720 tcaactttt gccttctaca aagcctgcca tgaaagtctt tctgcttcaa aatagactta      780
tttaaggata gttgtgtgaa ctactggtct ctcatttgtg agttattgca gtttgaattt      840
catgtcaatt tggttttata tgtaatttag taacctggga tatctcccat ggagaaaata      900
atccttggat cttgtttcca ttttggccat ttcagttaat aaagaaattc atttttttcca    960 aaaaaaaaaa aaaaaaa                                                     977
```

<210> SEQ ID NO 14
<211> LENGTH: 225
<212> TYPE: PRT
<213> ORGANISM: SOYBEAN

<400> SEQUENCE: 14

```
Met Ala Ala Asn Gln Glu Asp Val Lys Leu Leu Gly Ala Thr Gly Ser
  1               5                  10                  15

Pro Phe Val Cys Arg Val Gln Ile Ala Leu Lys Leu Lys Gly Val Gln
                 20                  25                  30

Tyr Lys Phe Leu Glu Glu Asn Leu Arg Asn Lys Ser Glu Leu Leu Leu
             35                  40                  45

Lys Ser Asn Pro Val His Lys Val Pro Val Phe Ile His Asn Glu
     50                   55                  60

Lys Pro Ile Ala Glu Ser Leu Val Ile Val Glu Tyr Ile Asp Glu Thr
 65                   70                  75                  80

Trp Lys Asn Asn Pro Ile Leu Pro Ser Asp Pro Tyr Gln Arg Ala Leu
                 85                  90                  95

Ala Arg Phe Trp Ser Lys Phe Ile Asp Asp Lys Val Val Gly Ala Ala
                100                 105                 110

Trp Lys Tyr Ile Tyr Thr Val Asp Glu Lys Glu Arg Glu Lys Asn Val
            115                 120                 125

Glu Glu Ser Tyr Glu Ala Leu Gln Phe Leu Glu Asn Glu Leu Lys Asp
        130                 135                 140

Lys Lys Phe Phe Gly Gly Glu Glu Ile Gly Leu Val Asp Ile Ala Ala
145                 150                 155                 160

Val Phe Ile Ala Phe Trp Ile Pro Ile Ile Gln Glu Val Leu Gly Leu
                165                 170                 175

Lys Leu Phe Thr Ser Glu Lys Phe Pro Lys Leu Tyr Lys Trp Ser Gln
            180                 185                 190

Glu Phe Ile Asn His Pro Val Val Lys Gln Val Leu Pro Pro Arg Asp
        195                 200                 205

Gln Leu Phe Ala Phe Tyr Lys Ala Cys His Glu Ser Leu Ser Ala Ser
    210                 215                 220

Lys
225
```

<210> SEQ ID NO 15
<211> LENGTH: 1006
<212> TYPE: DNA
<213> ORGANISM: SOYBEAN

-continued

```
<400> SEQUENCE: 15
atagtgctgc aatggcttca agtcaggagg aggtgaccct tttgggagct actggaagcc      60
catttgtgtg cagggttcat attgccctca agttgaaggg agttcaatac aaatatgtcg     120
aagaaaattt gaggaacaag agtgaactgc ttctcaaatc caacccagtt cacaagaagg     180
ttccagtgtt tattcacaat gagaagccca tagcagagtc tcttgtgatt gttgaataca     240
ttgatgagac atggaagaac aaccccatct tgccttctga tccttaccaa agagccttgg     300
ctcgtttctg gtccaaattc attgatgata aggttttttgg tgctgcatgg aaatccgttt     360
tcacagctga tgagaaagag cgtgagaaga atgttgagga agcaattgag ctctgcagtt     420
tcttgagaat gagataaagg acaagaagtt ctttggagga gaggagattg ggttggtaga     480
tattgctgct gtctacatag cattttgggt ccctatggtt caagaaattg cagggttgga     540
gttattcaca agtgagaaat ttcctaagct ccacaattgg agccaagaat ttttgaacca     600
tccaattgtc aaagaaagtc tgcccctag agatcctgtt ttctcctttt tcaagggtct     660
ctatgaaagc cttttttggtt caaaatagat ttgatgatgt ggtgtgagac ttagtatttc     720
taagaattat gtgtttgtta aaggcttcta tgaaagcctc actgcttcaa aatagattca     780
tgtatgtgag actcagaatc tctggggaaa attgtgtgtg gtgtggacta cttgttttgt     840
ttgtcattga gctatatcgc tgttaattag gattttgttt caaaatgatg cttataagtt     900
gtaatctagg atttctcccct ttgaaatcct aggttgttct tgacatttgc tatttcaaag     960
aataaatata tagcatcttt ctatttctca aaaaaaaaa aaaaaa                    1006
```

<210> SEQ ID NO 16
<211> LENGTH: 225
<212> TYPE: PRT
<213> ORGANISM: SOYBEAN

<400> SEQUENCE: 16

```
Met Ala Ser Ser Gln Glu Glu Val Thr Leu Leu Gly Ala Thr Gly Ser
  1               5                  10                  15

Pro Phe Val Cys Arg Val His Ile Ala Leu Lys Leu Lys Gly Val Gln
                 20                  25                  30

Tyr Lys Tyr Val Glu Glu Asn Leu Arg Asn Lys Ser Glu Leu Leu Leu
             35                  40                  45

Lys Ser Asn Pro Val His Lys Lys Val Pro Val Phe Ile His Asn Glu
         50                  55                  60

Lys Pro Ile Ala Glu Ser Leu Val Ile Val Glu Tyr Ile Asp Glu Thr
     65                  70                  75                  80

Trp Lys Asn Asn Pro Ile Leu Pro Ser Asp Pro Tyr Gln Arg Ala Leu
                 85                  90                  95

Ala Arg Phe Trp Ser Lys Phe Ile Asp Asp Lys Val Phe Gly Ala Ala
                100                 105                 110

Trp Lys Ser Val Phe Thr Ala Asp Glu Lys Glu Arg Glu Lys Asn Val
            115                 120                 125

Glu Glu Ala Ile Glu Ala Leu Gln Phe Leu Glu Asn Glu Ile Lys Asp
        130                 135                 140

Lys Lys Phe Phe Gly Gly Glu Glu Ile Gly Leu Val Asp Ile Ala Ala
145                 150                 155                 160

Val Tyr Ile Ala Phe Trp Val Pro Met Val Gln Glu Ile Ala Gly Leu
                165                 170                 175

Glu Leu Phe Thr Ser Glu Lys Phe Pro Lys Leu His Asn Trp Ser Gln
            180                 185                 190
```

-continued

```
Glu Phe Leu Asn His Pro Ile Val Lys Glu Ser Leu Pro Pro Arg Asp
            195                 200                 205

Pro Val Phe Ser Phe Phe Lys Gly Leu Tyr Glu Ser Leu Phe Gly Ser
    210                 215                 220

Lys
225
```

<210> SEQ ID NO 17
<211> LENGTH: 993
<212> TYPE: DNA
<213> ORGANISM: SOYBEAN

<400> SEQUENCE: 17

```
agctagttca cagcttcagt tcgttttttgt tgatcctgtg aacttatggc tgacggggtg      60
gttctgttgg atacatgggc cagcatgttt gggatgaggg ttaggattgc attagctgaa     120
aagggtgttg agtatgaata caaggaagaa aatctcagga caagagtcc tttgcttttg      180
caaatgaacc caattcacaa gaaaattcca gttctgatcc ataatggcaa accaatttgt     240
gaatctgcaa ttatagtgca gtacattgat gaggtctgga atgataaagc tccaatcttg     300
ccctctgacc cttatgagag agctcaagcc agattctggg tagattacat tgacaaaaag     360
gtgtatgaca cttggaggaa aatgtggctt tctaaaggag aggagcatga ggcagggaag     420
aaggagttta tctctatctt taagcagcta gaagagacac tgagtgacaa agcttattat     480
ggaagtgaca cctttgggtt ccttgatatt ggtttgatcc cttctacag ttggttttat      540
acctttgaga catatggtaa cttcaaaatg gaagaagagt gtcctaaact cgttgcttgg     600
gctaagagat gcatgcaaag agaggctgtg tccaaatctc tttcctgatg agaagaaggt     660
gtatgactat gttgtggccg taacaaaatt acttgagtca aactagagag acttcttgaa     720
taaattcacg taaggtcttg tgtaattttt atcttatgtt tgcttgggag ttacttatag     780
cttcctagac acttgagtgt gtctagtgtc tgcaggattt gtaactttat cttatgtttg     840
ctagccttca gttacttatg attgctagac ccttgagtgt gtctacagga tttggagctg     900
aggaaggatg gatgttgtaa tgtttgtttt aagttgtgtg tttatgatca ataaatcact     960
cattttataa ggacaaaaaa aaaaaaaaaa aaa                                  993
```

<210> SEQ ID NO 18
<211> LENGTH: 200
<212> TYPE: PRT
<213> ORGANISM: SOYBEAN

<400> SEQUENCE: 18

```
Met Ala Asp Gly Val Val Leu Leu Asp Thr Trp Ala Ser Met Phe Gly
  1               5                  10                  15

Met Arg Val Arg Ile Ala Leu Ala Glu Lys Gly Val Glu Tyr Glu Tyr
             20                  25                  30

Lys Glu Glu Asn Leu Arg Asn Lys Ser Pro Leu Leu Leu Gln Met Asn
         35                  40                  45

Pro Ile His Lys Lys Ile Pro Val Leu Ile His Asn Gly Lys Pro Ile
     50                  55                  60

Cys Glu Ser Ala Ile Ile Val Gln Tyr Ile Asp Glu Val Trp Asn Asp
 65                  70                  75                  80

Lys Ala Pro Ile Leu Pro Ser Asp Pro Tyr Glu Arg Ala Gln Ala Arg
                 85                  90                  95

Phe Trp Val Asp Tyr Ile Asp Lys Lys Val Tyr Asp Thr Trp Arg Lys
            100                 105                 110
```

```
Met Trp Leu Ser Lys Gly Glu Glu His Glu Ala Gly Lys Lys Glu Phe
        115                 120                 125
Ile Ser Ile Phe Lys Gln Leu Glu Glu Thr Leu Ser Asp Lys Ala Tyr
        130                 135                 140
Tyr Gly Ser Asp Thr Phe Gly Phe Leu Asp Ile Gly Leu Ile Pro Phe
145                 150                 155                 160
Tyr Ser Trp Phe Tyr Thr Phe Gly Thr Tyr Gly Asn Phe Lys Met Glu
                165                 170                 175
Glu Glu Cys Pro Lys Leu Val Ala Trp Ala Lys Arg Cys Met Gln Arg
            180                 185                 190
Glu Ala Val Ser Lys Ser Leu Ser
        195                 200

<210> SEQ ID NO 19
<211> LENGTH: 935
<212> TYPE: DNA
<213> ORGANISM: SOYBEAN

<400> SEQUENCE: 19
attttcttca tccttctctg ttctcctaga acttgattac ttgaacattc cctatgacag    60
atgaggtggt tcttctggat ttctggccaa gtccatttgg gatgagggtc aggattgcac   120
ttgctgaaaa gggtatcgaa tatgagtaca agaagagga cttgaggaac aagagtcctc    180
ttctcttaca aatgaacccg gttcacaaga agattccggt tctcatccac aatggcaaac   240
ccatttccga atccctcatt gctgttcagt acattgagga ggtttggaat gacagaaatc    300
ccttgttgcc ttcagaccct taccagagag ctcaggctag attctgggct gattatgttg    360
acattaagat acatgatctt ggaaagaaat ttggacatca aagggagaag aaaaagaagc    420
tgccaagaag gagttcatag aggcccttaa attgttggag gaacagctgg gagataagac    480
ttattttgga ggagacaata ttggttttgt ggatatagca cttgttccat tctacacttg    540
gttcaaagtc tatgagactt ttggcagcct caacattgag aatgagtgcc ccaggtttgt    600
tgcttgggcc aagaggtgcc tacagaaaga gagtgttgca aagtctcttc ctgatcagca    660
caaggtctat gagttcgttg tggagataag aaagaagtta gtcatcgagt aggtttcatg    720
ttggatctta atagccatag tgaagtattg gtcgttcttg acctttcaac taaataatat    780
ttgtgtaata aaaaggcatt tggatgtgcc aaacttcatg ctttctgttg gattgtgtag    840
gtttttaaaat ttttctgatg tatctttcat gtgtttgttg gttttgcaat agagtatttt    900
ccgtattatc atataaaaaa aaaaaaaaaa aaaaa                               935

<210> SEQ ID NO 20
<211> LENGTH: 219
<212> TYPE: PRT
<213> ORGANISM: SOYBEAN

<400> SEQUENCE: 20

Met Thr Asp Glu Val Val Leu Leu Asp Phe Trp Pro Ser Pro Phe Gly
1               5                   10                  15
Met Arg Val Arg Ile Ala Leu Ala Glu Lys Gly Ile Glu Tyr Glu Tyr
            20                  25                  30
Lys Glu Glu Asp Leu Arg Asn Lys Ser Pro Leu Leu Leu Gln Met Asn
        35                  40                  45
Pro Val His Lys Lys Ile Pro Val Leu Ile His Asn Gly Lys Pro Ile
    50                  55                  60
```

Ser Glu Ser Leu Ile Ala Val Gln Tyr Ile Glu Val Trp Asn Asp
 65                  70                  75                  80

Arg Asn Pro Leu Leu Pro Ser Asp Pro Tyr Gln Arg Ala Gln Ala Arg
                 85                  90                  95

Phe Trp Ala Asp Tyr Val Asp Ile Lys Ile His Asp Leu Gly Lys Lys
            100                 105                 110

Ile Trp Thr Ser Lys Gly Glu Glu Lys Glu Ala Lys Lys Glu Phe
        115                 120                 125

Ile Glu Ala Leu Lys Leu Leu Glu Glu Gln Leu Gly Asp Lys Thr Tyr
    130                 135                 140

Phe Gly Gly Asp Asn Ile Gly Phe Val Asp Ile Ala Leu Val Pro Phe
145                 150                 155                 160

Tyr Thr Trp Phe Lys Val Tyr Glu Thr Phe Gly Ser Leu Asn Ile Glu
                165                 170                 175

Asn Glu Cys Pro Arg Phe Val Ala Trp Ala Lys Arg Cys Leu Gln Lys
            180                 185                 190

Glu Ser Val Ala Lys Ser Leu Pro Asp Gln His Lys Val Tyr Glu Phe
        195                 200                 205

Val Val Glu Ile Arg Lys Lys Leu Val Ile Glu
    210                 215

<210> SEQ ID NO 21
<211> LENGTH: 895
<212> TYPE: DNA
<213> ORGANISM: SOYBEAN

<400> SEQUENCE: 21
aaataagtat cttcgtagtt gcataagtca agagaagaag tgaagtggct gcaatggctt      60
caagtcagga agaggtgacc cttttgggag ttgtgggaag cccatttcta cacagggttc     120
agattgctct caagttgaag ggagttgaat acaaatattt ggaagacgat ttgaacaaca     180
agagtgattt gctcctcaag tataacccag tttacaaaat gattccagtg cttgttcaca     240
atgagaagcc catttcagag tcccttgtga ttgttgagta cattgatgac acatggaaaa     300
acaatcccat cttgccttct gatccctacc aaagagcctt ggctcgtttc tgggctaagt     360
tcattgatga caagtgtgtg gttccagcat ggaaatctgc ttttatgact gatgagaaag     420
agaaagagaa ggctaaagaa gagttatttg aggctctgag ttttcttgag aatgagttga     480
agggcaagtt ttttggtgga gaggagtttg gctttgtgga tattgctgct gtgttaatac     540
ctataattca agagatagca gggttgcaat tgttcacaag tgagaaattc ccaaagctct     600
ctaaatggag ccaagacttt cacaaccatc cagttgtcaa cgaagttatg cctcctaagg     660
atcaactttt tgcctatttc aaggctcggg ctcaaagctt cgttgctaaa gaaagaatt      720
aatatagtga gactcagaat ttccatcgag gtttcagtat tgtatgaaat gaaagctact     780
tgtctatgtt tcgttattgc ggttgtattt tcatttttca atgaattatg tgatataga     840
tttctccatg tcaaaagata gttcaattca atcaataaaa taaacgaatg agcgg          895

<210> SEQ ID NO 22
<211> LENGTH: 222
<212> TYPE: PRT
<213> ORGANISM: SOYBEAN

<400> SEQUENCE: 22

Met Ala Ser Ser Gln Glu Glu Val Thr Leu Leu Gly Val Val Gly Ser
  1               5                  10                  15

```
Pro Phe Leu His Arg Val Gln Ile Ala Leu Lys Leu Lys Gly Val Glu
         20                  25                  30

Tyr Lys Tyr Leu Glu Asp Asp Leu Asn Asn Lys Ser Asp Leu Leu Leu
     35                  40                  45

Lys Tyr Asn Pro Val Tyr Lys Met Ile Pro Val Leu Val His Asn Glu
 50                  55                  60

Lys Pro Ile Ser Glu Ser Leu Val Ile Val Glu Tyr Ile Asp Asp Thr
 65                  70                  75                  80

Trp Lys Asn Asn Pro Ile Leu Pro Ser Asp Pro Tyr Gln Arg Ala Leu
                 85                  90                  95

Ala Arg Phe Trp Ala Lys Phe Ile Asp Asp Lys Cys Val Val Pro Ala
             100                 105                 110

Trp Lys Ser Ala Phe Met Thr Asp Glu Lys Glu Lys Glu Lys Ala Lys
         115                 120                 125

Glu Glu Leu Phe Glu Ala Leu Ser Phe Leu Glu Asn Glu Leu Lys Gly
     130                 135                 140

Lys Phe Phe Gly Gly Glu Gly Phe Gly Phe Val Asp Ile Ala Ala Val
145                 150                 155                 160

Leu Ile Pro Ile Ile Gln Glu Ile Ala Gly Leu Gln Leu Phe Thr Ser
                 165                 170                 175

Glu Lys Pro Lys Leu Ser Lys Trp Ser Gln Asp Phe His Asn His
             180                 185                 190

Pro Val Val Asn Glu Val Met Pro Pro Lys Asp Gln Leu Phe Ala Tyr
         195                 200                 205

Phe Lys Ala Arg Ala Gln Ser Phe Val Ala Lys Arg Lys Asn
     210                 215                 220

<210> SEQ ID NO 23
<211> LENGTH: 885
<212> TYPE: DNA
<213> ORGANISM: SOYBEAN

<400> SEQUENCE: 23
ccatagcaat ggcagagcaa gacaaggtga tcctacacgg gatgtgggcc agcccttatg     60
ccaagagggt ggaattggcc cttaatttta agggcatacc ctatgagtat gttgaagaag    120
acttgagaaa taagagtgat ttgcttctaa agtacaaccc tgttcacaag aaggttcctg    180
tacttgttca taatggaaag gccattgctg aatccatggt gatccttgag tatattgatg    240
aaacatggaa agatggtcct aaactgcttc caagtgattc ttacaaacga gcccaagctc    300
gattctggtg tcatttcatc caggatcagt taatggagag cacttttcta gtagtcaaaa    360
ctgatggaga agcacaacaa aaggccattg accacgtgta tgagaaactg aaagtgctag    420
aagatggaat gaagacctat ctgggagaag gcaatgctat tatctctggt gttgaaaaca    480
actttggaat ccttgacatt gtgttttgtg ctttatatgg tgcctacaag gctcatgaag    540
aagttattgg cctcaagttc atagtgccag aaaagtttcc tgtgttgttt tcttggttga    600
tggctattgc tgaggttgaa gctgtgaaaa ttgcaactcc tccacatgaa aaacagtgg    660 gaattcttca gttgttcagg ctgtctgcac tgaaatcttc ttctgccaca gaatgatata    720
tacttcaaca ctttaataga ctgtccatcg tttgcttctt ctgcgagtct ttagtgtatg    780
tatctttcaa taacaggatg agtaacacct gagtatgtaa agcgtgatga tatagagata    840
tacctctata tatcaaatac tcttctataa aaaaaaaaa aaaaa               885
```

<210> SEQ ID NO 24
<211> LENGTH: 235
<212> TYPE: PRT
<213> ORGANISM: SOYBEAN

<400> SEQUENCE: 24

```
Met Ala Glu Gln Asp Lys Val Ile Leu His Gly Met Trp Ala Ser Pro
  1               5                  10                  15
Tyr Ala Lys Arg Val Glu Leu Ala Leu Asn Phe Lys Gly Ile Pro Tyr
                 20                  25                  30
Glu Tyr Val Glu Glu Asp Leu Arg Asn Lys Ser Asp Leu Leu Leu Lys
             35                  40                  45
Tyr Asn Pro Val His Lys Lys Val Pro Val Leu Val His Asn Gly Lys
     50                  55                  60
Ala Ile Ala Glu Ser Met Val Ile Leu Glu Tyr Ile Asp Glu Thr Trp
 65                  70                  75                  80
Lys Asp Gly Pro Lys Leu Leu Pro Ser Asp Ser Tyr Lys Arg Ala Gln
                 85                  90                  95
Ala Arg Phe Trp Cys His Phe Ile Gln Asp Gln Leu Met Glu Ser Thr
            100                 105                 110
Phe Leu Val Val Lys Thr Asp Gly Glu Ala Gln Gln Lys Ala Ile Asp
            115                 120                 125
His Val Tyr Glu Lys Leu Lys Val Leu Glu Asp Gly Met Lys Thr Tyr
    130                 135                 140
Leu Gly Glu Gly Asn Ala Ile Ile Ser Gly Val Glu Asn Asn Phe Gly
145                 150                 155                 160
Ile Leu Asp Ile Val Phe Cys Ala Leu Tyr Gly Ala Tyr Lys Ala His
                165                 170                 175
Glu Glu Val Ile Gly Leu Lys Phe Ile Val Pro Glu Lys Phe Pro Val
            180                 185                 190
Leu Phe Ser Trp Leu Met Ala Ile Ala Glu Val Glu Ala Val Lys Ile
            195                 200                 205
Ala Thr Pro Pro His Glu Lys Thr Val Gly Ile Leu Gln Leu Phe Arg
        210                 215                 220
Leu Ser Ala Leu Lys Ser Ser Ser Ala Thr Glu
225                 230                 235
```

<210> SEQ ID NO 25
<211> LENGTH: 991
<212> TYPE: DNA
<213> ORGANISM: SOYBEAN

<400> SEQUENCE: 25

```
ctcgtgccgt ttctataaag gccaaactca caaaccacac cctaacaaat tcatcttatt    60
ttgcaacaca attcaatttt gagcacttac caacaccact tccaatggct tcatatcatg   120
aagaagaagt gaggctattg gcaagtgggc cagcccatt tagcaacaga gtagaccttg    180
ctctcaagct caagggtgtt ccctacaaat actccgagga agatcttgct aacaagagtg   240
ctgatcttct caagtacaac cccgttcaca agaaggttcc ggttttggtc cacaatggga   300
acccattgcc cgagtcactc atcattgttg aatacataga tgagacgtgg aaaaataacc   360
cactattgcc tcaagaccca tatgaaagag ccttggctcg ttttggtct aagaccttag    420
atgacaagat cttgccagct atatggaatg cttgctggag tgacgagaat gggcgtgaga   480
aagcagtgga ggaagccttg gaagcattga aaatcctaca ggaaacactg aaagacaaga   540
aattctttgg aggagagagc ataggattgg tagatattgc tgccaatttc attgggtatt   600
```

-continued

```
gggttgccat attgcaagag attgcagggt tggagttgct caccattgag aaatttccca      660
agttatataa ttggagtcaa gactttatca accaccctgt gatcaaggag ggtctgcctc      720
ctagagatga attgtttgct ttcttcaaag cttctgctaa aaagtagaac cattttagag      780
gtaggattca taataagtta gtatgatttt gttgggaaac aattatcttg ttgtgagcaa      840
aggattgttc tgttttaaat ttaattgact gtgatttggt tgggtattgg ctatttaat       900 tttaactaaa aaaagtgttc agttttaaaa aaaaaaaaaa aaaaaaaaaa aaaaaaaaa       960 aaaaaaaaaa aaaaaaaaaa aaaaaaaaaa a                                     991
```

<210> SEQ ID NO 26
<211> LENGTH: 220
<212> TYPE: PRT
<213> ORGANISM: SOYBEAN

<400> SEQUENCE: 26

```
Met Ala Ser Tyr His Glu Glu Val Arg Leu Leu Gly Lys Trp Ala
 1               5                  10                  15

Ser Pro Phe Ser Asn Arg Val Asp Leu Ala Leu Lys Leu Lys Gly Val
                20                  25                  30

Pro Tyr Lys Tyr Ser Glu Glu Asp Leu Ala Asn Lys Ser Ala Asp Leu
            35                  40                  45

Leu Lys Tyr Asn Pro Val His Lys Val Pro Val Leu Val His Asn
        50                  55                  60

Gly Asn Pro Leu Pro Glu Ser Leu Ile Ile Val Glu Tyr Ile Asp Glu
 65                  70                  75                  80

Thr Trp Lys Asn Asn Pro Leu Leu Pro Gln Asp Pro Tyr Glu Arg Ala
                85                  90                  95

Leu Ala Arg Phe Trp Ser Lys Thr Leu Asp Asp Lys Ile Leu Pro Ala
            100                 105                 110

Ile Trp Asn Ala Cys Trp Ser Asp Glu Asn Gly Arg Glu Lys Ala Val
        115                 120                 125

Glu Glu Ala Leu Glu Ala Leu Lys Ile Leu Gln Glu Thr Leu Lys Asp
    130                 135                 140

Lys Lys Phe Phe Gly Gly Glu Ser Ile Gly Leu Val Asp Ile Ala Ala
145                 150                 155                 160

Asn Phe Ile Gly Tyr Trp Val Ala Ile Leu Gln Glu Ile Ala Gly Leu
                165                 170                 175

Glu Leu Leu Thr Ile Glu Lys Phe Pro Lys Leu Tyr Asn Trp Ser Gln
            180                 185                 190

Asp Phe Ile Asn His Pro Val Ile Lys Glu Gly Leu Pro Pro Arg Asp
        195                 200                 205

Glu Leu Phe Ala Phe Phe Lys Ala Ser Ala Lys Lys
    210                 215                 220
```

<210> SEQ ID NO 27
<211> LENGTH: 1024
<212> TYPE: DNA
<213> ORGANISM: SOYBEAN

<400> SEQUENCE: 27

```
ccaaatctta aaatattca gtgaagatca acctcaatgg catctcttgg cgtgcgacca       60
gttcttcccc ctccattaac ttccatctcc gacccacctc tcttttcga tggcaccacc      120 aggttgtaca tcagttattc ttgccccctat gcacaacgtg tgtggatcgc taggaactac      180 aagggctac aagataagat caatttggtc cctattaacc ttcaagacag gccagcttgg      240
```

-continued

```
tataaggaga aagtctaccc tgaaaataag gtgccatcct tggagcacaa tggcaaggtg      300
ttgggagaaa gtcttgattt gatcaaatat gtagatgcaa actttgaagg gacacctttg      360
tttcccagtg atcctgccaa gaaagagttc ggtgagcaat tgatatccca tgttgataca      420
ttcagcaaag acctgttcgt ttcattgaaa ggggatgctg tacagcaagc cagtcccgct      480
tttgaatact tggagaatgc tcttggtaaa tttgatgatg gccattctt gcttggccaa       540 ttcagtttgg tggatattgc ttatattcca tttgttgaaa gattccaaat tgtctttgct      600
gaggtgttca acatgacat cacagaagga aggcctaaac ttgcaacatg gtttgaggag       660
ttgaataagc taaatgctta taccgagact agagtcgatc ctcaggagat cgttgatctt      720
ttcaagaaac gcttcctgcc tcaacagtga acgttgtatt gctgcaggct tcctctaaaa      780
tgtagactct gcccatatag cgtcctttca ttcacgggat gggatgcatc tgcagtcaaa      840
tgtcggttgt gtttatctgc cagagttgca ggatagtttg aagtcataat cacgttcatt      900
tttcagcttg tttgtttgat gtcataataa tgtttatgta ccagtttgtg atcactgatc      960
aatatgatat aatgaccaat atggtattat tatcctattt gaactaaaaa aaaaaaaaaa     1020
aaaa                                                                  1024
```

<210> SEQ ID NO 28
<211> LENGTH: 237
<212> TYPE: PRT
<213> ORGANISM: SOYBEAN

<400> SEQUENCE: 28

```
Met Ala Ser Leu Gly Val Arg Pro Val Leu Pro Pro Leu Thr Ser
  1               5                  10                  15

Ile Ser Asp Pro Pro Leu Phe Asp Gly Thr Thr Arg Leu Tyr Ile
                 20                  25                  30

Ser Tyr Ser Cys Pro Tyr Ala Gln Arg Val Trp Ile Ala Arg Asn Tyr
             35                  40                  45

Lys Gly Leu Gln Asp Lys Ile Asn Leu Val Pro Ile Asn Leu Gln Asp
         50                  55                  60

Arg Pro Ala Trp Tyr Lys Glu Val Tyr Pro Glu Asn Lys Val Pro
 65                  70                  75                  80

Ser Leu Glu His Asn Gly Lys Val Leu Gly Glu Ser Leu Asp Leu Ile
                 85                  90                  95

Lys Tyr Val Asp Ala Asn Phe Glu Gly Thr Pro Leu Phe Pro Ser Asp
                100                 105                 110

Pro Ala Lys Lys Glu Phe Gly Glu Gln Leu Ile Ser His Val Asp Thr
            115                 120                 125

Phe Ser Lys Asp Leu Phe Val Ser Leu Lys Gly Asp Ala Val Gln Gln
        130                 135                 140

Ala Ser Pro Ala Phe Glu Tyr Leu Glu Asn Ala Leu Gly Lys Phe Asp
145                 150                 155                 160

Asp Gly Pro Phe Leu Leu Gly Gln Phe Ser Leu Val Asp Ile Ala Tyr
                165                 170                 175

Ile Pro Phe Val Glu Arg Phe Gln Ile Val Phe Ala Glu Val Phe Lys
                180                 185                 190

His Asp Ile Thr Glu Gly Arg Pro Lys Leu Ala Thr Trp Phe Glu Glu
            195                 200                 205
```

```
Leu Asn Lys Leu Asn Ala Tyr Thr Glu Thr Arg Val Asp Pro Gln Glu
    210                 215                 220

Ile Val Asp Leu Phe Lys Lys Arg Phe Leu Pro Gln Gln
225                 230                 235

<210> SEQ ID NO 29
<211> LENGTH: 24
<212> TYPE: DNA
<213> ORGANISM: SOYBEAN
<220> FEATURE:
<221> NAME/KEY: unsure
<222> LOCATION: (3)
<223> OTHER INFORMATION: Y=C OR T
<221> NAME/KEY: unsure
<222> LOCATION: (6)
<223> OTHER INFORMATION: R=A OR G
<221> NAME/KEY: unsure
<222> LOCATION: (9)
<223> OTHER INFORMATION: N=G or A or T or C
<221> NAME/KEY: unsure
<222> LOCATION: (12)
<223> OTHER INFORMATION: N=G or A or T or C
<221> NAME/KEY: unsure
<222> LOCATION: (15)
<223> OTHER INFORMATION: N=G or A or T or C
<221> NAME/KEY: unsure
<222> LOCATION: (21)
<223> OTHER INFORMATION: Y=C OR T
<221> NAME/KEY: unsure
<222> LOCATION: (18)
<223> OTHER INFORMATION: Y=C OR T

<400> SEQUENCE: 29
gaygarganc tnctngaytt ytgg                                            24

<210> SEQ ID NO 30
<211> LENGTH: 19
<212> TYPE: DNA
<213> ORGANISM: SOYBEAN

<400> SEQUENCE: 30
gactcgagtc gacatgctt                                                  19

<210> SEQ ID NO 31
<211> LENGTH: 36
<212> TYPE: DNA
<213> ORGANISM: SOYBEAN

<400> SEQUENCE: 31
catatgagtg atgaggtagt gttattagat ttctgg                               36

<210> SEQ ID NO 32
<211> LENGTH: 34
<212> TYPE: DNA
<213> ORGANISM: SOYBEAN

<400> SEQUENCE: 32
ttattacaca aatattactt atttgaaagg ctaa                                 34

<210> SEQ ID NO 33
<211> LENGTH: 1117
<212> TYPE: DNA
<213> ORGANISM: SOYBEAN
<220> FEATURE:
<221> NAME/KEY: unsure
<222> LOCATION: (1101)
<223> OTHER INFORMATION: M=A OR C
<221> NAME/KEY: unsure
<222> LOCATION: (1104)
```

<223> OTHER INFORMATION: M=A OR C
<221> NAME/KEY: unsure
<222> LOCATION: (1116)
<223> OTHER INFORMATION: N=G or A or T or C

<400> SEQUENCE: 33

```
aaaaaaagag acacatacaa caacaaatgt attagagata tagaagaaac aaattaaagg      60
aattgaaatt aacttttgaa agaagatggg aagcgaagaa gtgaagctgt tgagcttttg     120
ggtgagtcca tttggtaaaa ggattgagtg ggctttgaaa ctgaagggtg tagagtatga     180
gtatatagaa gaagatatct tcaacaagag tagtctcctt ctggagttga acccggttca     240
caagaaggtt ccggttcttg ttcatgcaga aaaatccatc atcgctgaat cattcatcat     300
ccttgaatac atagatgaaa atggaagca atattcattg ttacctcatc atccttatca      360
aagagcactt gctcgctttt gggctgctac tgctgaagaa atgttcagga aggtagtatg     420
gattgctttg cgcagcccta ccagcgggga tgaacgcgag aaggctctta aggaatcgag     480
agaagtaatg gagagaatag aagaagagat taggggggaag aaatatttcg gaggggacaa    540
tattgggtac cttgacattg cacttggatg gatctcttac tggcttcctg ttttggagga    600
agttggatca atgcagataa tagatccatt gaaatttcca gccaccactg catggatgac    660
taatttttctc agcaatccag tgatcaagga caacttgccc ccaagagata agatgcttgt   720
ttacctcaaa gatctaagaa gcaaatatat agtcttataa ttaagatgca tgaattggtg    780
aaggactaga tttgttcctc caaatttatg tatgtgatac tttcaagata tttggattgg    840
tgtaaagcat cgggtcaaat ctctggctaa gttagcattt tctagattta ctcttttgaa    900
gtggctttga tctttgatgt caattatcct actcttatgt agcttaacta ataaatatat    960
ttatattgat ggcaataaat cataattcaa ttctttaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080
aaaaaaaaaa aacaaaaaaa maamaaaaaa aaaaana                             1117
```

<210> SEQ ID NO 34
<211> LENGTH: 224
<212> TYPE: PRT
<213> ORGANISM: SOYBEAN

<400> SEQUENCE: 34

```
Met Gly Ser Glu Glu Val Lys Leu Leu Ser Phe Trp Val Ser Phe
 1               5                  10                  15

Gly Lys Arg Ile Glu Trp Ala Leu Lys Leu Lys Gly Val Glu Tyr Glu
             20                  25                  30

Tyr Ile Glu Glu Asp Ile Phe Asn Lys Ser Ser Leu Leu Leu Glu Leu
         35                  40                  45

Asn Pro Val His Lys Lys Val Pro Val Leu Val His Ala Glu Lys Ser
     50                  55                  60

Ile Ile Ala Glu Ser Phe Ile Ile Leu Glu Tyr Ile Asp Lys Trp
 65                  70                  75                  80

Lys Gln Tyr Ser Leu Leu Pro His His Pro Tyr Gln Arg Ala Leu Ala
                 85                  90                  95

Arg Phe Trp Ala Ala Thr Ala Glu Glu Met Phe Arg Lys Val Val Trp
            100                 105                 110

Ile Ala Leu Arg Ser Pro Thr Ser Gly Asp Glu Arg Glu Lys Ala Leu
        115                 120                 125

Lys Glu Ser Arg Glu Val Met Glu Arg Ile Glu Glu Ile Arg Gly
    130                 135                 140
```

-continued

```
Lys Lys Tyr Phe Gly Gly Asp Asn Ile Gly Tyr Leu Asp Ile Ala Leu
145                 150                 155                 160

Gly Trp Ile Ser Tyr Trp Leu Pro Val Leu Glu Glu Val Gly Ser Met
                165                 170                 175

Gln Ile Ile Asp Pro Leu Lys Phe Pro Ala Thr Thr Ala Trp Met Thr
            180                 185                 190

Asn Phe Leu Ser Asn Pro Val Ile Lys Asp Asn Leu Pro Pro Arg Asp
        195                 200                 205

Lys Met Leu Val Tyr Leu Lys Asp Leu Arg Ser Lys Tyr Ile Val Leu
    210                 215                 220
```

<210> SEQ ID NO 35
<211> LENGTH: 1083
<212> TYPE: DNA
<213> ORGANISM: SOYBEAN

<400> SEQUENCE: 35

```
ctaaaggttg aagatttagc aaaacaatgg aagaagtgaa gctgattgct acacatcaaa    60
gcttcccttg tgccagggta gaatgggctt aaggataaaa aggtgttgaa tatgagtact   120
taaaagaaga cttagcaaat aagagttctt tgcttcttca atctaaccct gtccacaaga   180
aagttccagt gctcctacat aataacaagc tatagctga atcacttgtc atcctggagt    240
acatagatga gacatggaag aagaacccct tgctaccact tgatccatat gagagagcac   300
aggctcgctt ctgggctagg tttattgatg agaagtgtgt gttagctgta tggggagcta   360
ccgtggcgca aggagaagag aaagagaaag ctgtgggtgc tgcactagag tctctggcac   420
ttcttgagaa ggaaattcaa gggaagaagt attttggtgg agagaagatt ggttatcttg   480
atattgcagc tggctgcatg tctctttggt tcagtgtcct ggaagagctt ggagagatgg   540
agctactcaa tgctgagagg ttcccttctc ttcatgaatg gagtcagaac ttcttacaga   600
cttcacctgt caaagattgc attccatcca gggaaagtgt ggttgaatat ttcagctttg   660
gcatcaacta tgtgcgttcc ttagcagcat ccagtaaatc ttgaaactga aaatatacct   720
ttaatcaact acatgcatca tttataattg ttcacattgt ttgtattgga attggagttt   780
ggcttcaaat agtgttggtt atcttatcat atgtagttgt gtgaaatgtg taatcagttt   840
tctgtgcaat ggtggcacta ctagctatag tgaaattttc agttagctat gctatattgt   900
ggtttcatgt gacaatgcaa ttaatagtag tttattatcg gttcctgagg agagaaagaa   960
agaaagtttt cttttgttct gtatggctaa ttcagcagta agatagata ctgcttaaat    1020
agaagaaaaa caaagtacat taatcctttg ttcgcctatt tgaataaaaa aaaaaaaaaa  1080
aaa                                                                1083
```

<210> SEQ ID NO 36
<211> LENGTH: 225
<212> TYPE: PRT
<213> ORGANISM: SOYBEAN

<400> SEQUENCE: 36

```
Met Glu Glu Val Lys Leu Ile Ala Thr His Gln Ser Phe Pro Cys Ala
1               5                   10                  15

Arg Val Glu Trp Ala Leu Arg Ile Lys Gly Val Glu Tyr Glu Tyr Leu
                20                  25                  30

Lys Glu Asp Leu Ala Asn Lys Ser Ser Leu Leu Leu Gln Ser Asn Pro
            35                  40                  45
```

```
Val His Lys Lys Val Pro Val Leu Leu His Asn Asn Lys Pro Ile Ala
     50                  55                  60
Glu Ser Leu Val Ile Leu Glu Tyr Ile Asp Glu Thr Trp Lys Lys Asn
 65                  70                  75                  80
Pro Leu Leu Pro Leu Asp Pro Tyr Glu Arg Ala Gln Ala Arg Phe Trp
                 85                  90                  95
Ala Arg Phe Ile Asp Glu Lys Cys Val Leu Ala Val Trp Gly Ala Thr
                100                 105                 110
Val Ala Gln Gly Glu Glu Lys Glu Lys Ala Val Gly Ala Ala Leu Glu
                115                 120                 125
Ser Leu Ala Leu Leu Glu Lys Glu Ile Gln Gly Lys Lys Tyr Phe Gly
    130                 135                 140
Gly Glu Lys Ile Gly Tyr Leu Asp Ile Ala Ala Gly Cys Met Ser Leu
145                 150                 155                 160
Trp Phe Ser Val Leu Glu Glu Leu Gly Glu Met Glu Leu Leu Asn Ala
                165                 170                 175
Glu Arg Phe Pro Ser Leu His Glu Trp Ser Gln Asn Phe Leu Gln Thr
                180                 185                 190
Ser Pro Val Lys Asp Cys Ile Pro Ser Arg Glu Ser Val Val Glu Tyr
    195                 200                 205
Phe Ser Phe Gly Ile Asn Tyr Val Arg Ser Leu Ala Ala Ser Ser Lys
    210                 215                 220
Ser
225

<210> SEQ ID NO 37
<211> LENGTH: 855
<212> TYPE: DNA
<213> ORGANISM: SOYBEAN

<400> SEQUENCE: 37
tcatatcaca tccaaaatgg cctccaaatc agatattcac ctctacacta gccaaactcc      60
taacgggatc aagatctcca tcaccttgga agaactcggg cttTcatatg aggtgcacaa     120
gattgatata tccaagaaca ctcagaaaga gccatggttc ctcgagatta accctaatgg     180
acgcattccc gctttgacag atacgttcac ggatgggaag cagattaatt tattcgaaag     240
tggtagcatc aacagtacc ttgtcgacag atatgacaca gagcacaaga tctcatatcc     300
tagagggaca agagagtact atgaagtcaa caactggctc ttcttcctta cgctggagt     360
gggtcctatg caaggccaag ccaatcactt cagcaaatat gctcctgaga agattgagta     420
tggtatcaat cgctacttaa atgagaccag gcgtttgtat tccgtcctca atactcatct     480
cgaaaagtcc acctctggtt atttggttgg tgacagatgt acaatcgctg acattgctca     540
ctgggggtgg gtaactgcgg cgttttattg tggagttgac attgaagaat ttccagcttt     600
gaaggcatgg gacgagagaa tggagaagag accagcagta gagaaagggc gccacgtacc     660
agaaccacac aatatcggag cactgaagaa agaccctgaa cgtgaagcga agatgaaggc     720
tgcagctgaa aagaacagag aatggataca ggctggcatg aaaagtgatg ccaagaagta     780
atgcatctgc aaaagtcgag tatagcaaga actaaattca gtaaacaaat cctcattaaa     840
aaaaaaaaaa aaaaa                                                      855

<210> SEQ ID NO 38
<211> LENGTH: 254
<212> TYPE: PRT
<213> ORGANISM: SOYBEAN
```

<400> SEQUENCE: 38

```
Met Ala Ser Lys Ser Asp Ile His Leu Tyr Thr Ser Gln Thr Pro Asn
  1               5                  10                  15
Gly Ile Lys Ile Ser Ile Thr Leu Glu Glu Leu Gly Leu Ser Tyr Glu
                 20                  25                  30
Val His Lys Ile Asp Ile Ser Lys Asn Thr Gln Lys Glu Pro Trp Phe
             35                  40                  45
Leu Glu Ile Asn Pro Asn Gly Arg Ile Pro Ala Leu Thr Asp Thr Phe
 50                  55                  60
Thr Asp Gly Lys Gln Ile Asn Leu Phe Glu Ser Gly Ser Ile Gln Gln
 65                  70                  75                  80
Tyr Leu Val Asp Arg Tyr Asp Thr Glu His Lys Ile Ser Tyr Pro Arg
                 85                  90                  95
Gly Thr Arg Glu Tyr Tyr Glu Val Asn Asn Trp Leu Phe Phe Leu Asn
                100                 105                 110
Ala Gly Val Gly Pro Met Gln Gly Gln Ala Asn His Phe Ser Lys Tyr
            115                 120                 125
Ala Pro Glu Lys Ile Glu Tyr Gly Ile Asn Arg Tyr Leu Asn Glu Thr
130                 135                 140
Arg Arg Leu Tyr Ser Val Leu Asn Thr His Leu Glu Lys Ser Thr Ser
145                 150                 155                 160
Gly Tyr Leu Val Gly Asp Arg Cys Thr Ile Ala Asp Ile Ala His Trp
                165                 170                 175
Gly Trp Val Thr Ala Ala Phe Tyr Cys Gly Val Asp Ile Glu Glu Phe
                180                 185                 190
Pro Ala Leu Lys Ala Trp Asp Glu Arg Met Glu Lys Arg Pro Ala Val
            195                 200                 205
Glu Lys Gly Arg His Val Pro Glu Pro His Asn Ile Gly Ala Leu Lys
210                 215                 220
Lys Asp Pro Glu Arg Glu Ala Lys Met Lys Ala Ala Glu Lys Asn
225                 230                 235                 240
Arg Glu Trp Ile Gln Ala Gly Met Lys Ser Asp Ala Lys Lys
                245                 250
```

<210> SEQ ID NO 39
<211> LENGTH: 880
<212> TYPE: DNA
<213> ORGANISM: SOYBEAN

<400> SEQUENCE: 39

| | | | | | |
|---|---|---|---|---|---|
| catcatcacc | tccggtatct | caacacgaca | atctcttcag | aattaccaat | cgaaactcac | 60 |
| aaaatggtac | tcaaactcta | tggtatggct | cgagcaactt | gcactcagcg | agtactcact | 120 |
| gtactcgctg | agaaagacat | cgattacgag | ctcatctctg | tgaatatctt | ccagggagag | 180 |
| cagaagcagc | cttcgtggct | tgagaagcac | cctttcggaa | aggtcccctt | gctcgatgat | 240 |
| gatggttttt | tgatttatga | gagcagagcc | atatgcaaat | atcttgcacg | aaagtacgct | 300 |
| gataagggta | cgaaacttat | tcccgccgac | ggagatttaa | aagcctatgg | gctattcgaa | 360 |
| caagcttgct | cattggaaca | gtcttacttc | gatgttggta | gctttggtgt | ctggtttgaa | 420 |
| catgtcatca | agcaagtgaa | aggattgggc | gccaccagcc | cggaagctgt | tcaacaacat | 480 |
| ctccagggac | tcgaaaagac | tatcgctgca | tacgaccaaa | tactctcgaa | acaaaagtat | 540 |
| ctcgcgggag | atgagctcac | tttggctgat | ttgtaccatt | tgccacatgg | tacgcaggca | 600 |
| ttgacatggg | gactccaaga | catacttgga | aagtatcctc | acgtgaacag | gtggtgggag | 660 |

| | |
|---|---|
| gaacttcaag ctagagaaag ctggaaagga gtagttgcag ccgctgttta gatttatcat | 720 |
| gtgcttttgc tgtggtatac tattgtcaaa agacagccag ccatttttaat gggttgaggt | 780 |
| tgcatgcgtt tcagtcattc aaaatactag cactgccagt gataaaaatc ttattaccct | 840 |
| caaaaaaaaa aaaaaaaaaa aaaaaaaaaa aaaaaaaaaa | 880 |

<210> SEQ ID NO 40
<211> LENGTH: 215
<212> TYPE: PRT
<213> ORGANISM: SOYBEAN

<400> SEQUENCE: 40

Met Val Leu Lys Leu Tyr Gly Met Ala Arg Ala Thr Cys Thr Gln Arg
 1               5                  10                  15

Val Leu Thr Val Leu Ala Glu Lys Asp Ile Asp Tyr Glu Leu Ile Ser
             20                  25                  30

Val Asn Ile Phe Gln Gly Glu Gln Lys Gln Pro Ser Trp Leu Glu Lys
         35                  40                  45

His Pro Phe Gly Lys Val Pro Leu Leu Asp Asp Gly Phe Leu Ile
     50                  55                  60

Tyr Glu Ser Arg Ala Ile Cys Lys Tyr Leu Ala Arg Lys Tyr Ala Asp
 65                  70                  75                  80

Lys Gly Thr Lys Leu Ile Pro Ala Asp Gly Asp Leu Lys Ala Tyr Gly
                 85                  90                  95

Leu Phe Glu Gln Ala Cys Ser Leu Glu Gln Ser Tyr Phe Asp Val Gly
            100                 105                 110

Ser Phe Gly Val Trp Phe Glu His Val Ile Lys Gln Val Lys Gly Leu
        115                 120                 125

Gly Ala Thr Ser Pro Glu Ala Val Gln Gln His Leu Gln Gly Leu Glu
    130                 135                 140

Lys Thr Ile Ala Ala Tyr Asp Gln Ile Leu Ser Lys Gln Lys Tyr Leu
145                 150                 155                 160

Ala Gly Asp Glu Leu Thr Leu Ala Asp Leu Tyr His Leu Pro His Gly
                165                 170                 175

Thr Gln Ala Leu Thr Trp Gly Leu Gln Asp Ile Leu Gly Lys Tyr Pro
            180                 185                 190

His Val Asn Arg Trp Trp Glu Glu Leu Gln Ala Arg Glu Ser Trp Lys
        195                 200                 205

Gly Val Val Ala Ala Ala Val
    210                 215

<210> SEQ ID NO 41
<211> LENGTH: 951
<212> TYPE: DNA
<213> ORGANISM: SOYBEAN

<400> SEQUENCE: 41

| | |
|---|---|
| cttttcaaga gaatcaaacc atggcagtga agtatacgg tccccactgt gcttccacca | 60 |
| agcgggtgct ggtttgtctg gttgagaagg aagtcgaatt tgaggttgtc cctgttgatg | 120 |
| tcactaaggg ggagcagaag gatcctgagt acctcaaact acagccattt ggagttgttc | 180 |
| ctgtcatcaa agatggagat tataccttat atgaatctcg tgctataatg aggtattatg | 240 |
| cagaaaaata cagatctcaa ggggttgagt tgctgggaaa acaatagaa gagagggtc | 300 |
| tagtggagca atggctagaa gttgaagcac acaactttca tccacaagcc tacaacttgt | 360 |
| gtcttcatgg tttgtttggt tcactatttg gtgtgactcc agatcccaag gtgattgagg | 420 |

-continued

```
agagtgaagc aaagctggta caagtgttga acatctatga ggagaggctc tcaaagacta    480
agtatttggc tggggatttc ttcagcattg ctgatattag ccaccttcca tttcttgatt    540
atgttgtgaa caatatgggg aaaaagtatt tgttagagga gaggaagcat gtgggtgcct    600
ggtgggatga cattagcagt agaccatcat ggaacaaggt tctccagctc tacagagctc    660
caatctagtt gctaaatgag tttcagggaa actgctatta gtgtatcatc tttgaatatg    720
ttagtcaaga ataaatgtac ttttagcaga ttccaatgaa aggaagaaag tgggtagtgt    780
tcaacttaat ggaatgtgtt gaatttctgc tttctttcat tttcagttgt ttgcttgtgt    840
ttaatttgga tattccttgt ggtcatgctc ttaactttcc cgttgtttac cctctatttt    900
tcttttgcta ctgaataaaa gttatatata tataaaaaaa aaaaaaaaa a              951
```

<210> SEQ ID NO 42
<211> LENGTH: 215
<212> TYPE: PRT
<213> ORGANISM: SOYBEAN

<400> SEQUENCE: 42

```
Met Ala Val Lys Val Tyr Gly Pro His Cys Ala Ser Thr Lys Arg Val
  1               5                  10                  15

Leu Val Cys Leu Val Glu Lys Glu Val Glu Phe Glu Val Val Pro Val
             20                  25                  30

Asp Val Thr Lys Gly Glu Gln Lys Asp Pro Glu Tyr Leu Lys Leu Gln
         35                  40                  45

Pro Phe Gly Val Val Pro Val Ile Lys Asp Gly Asp Tyr Thr Leu Tyr
     50                  55                  60

Glu Ser Arg Ala Ile Met Arg Tyr Tyr Ala Glu Lys Tyr Arg Ser Gln
 65                  70                  75                  80

Gly Val Glu Leu Leu Gly Lys Thr Ile Glu Glu Arg Gly Leu Val Glu
                 85                  90                  95

Gln Trp Leu Glu Val Glu Ala His Asn Phe His Pro Gln Ala Tyr Asn
            100                 105                 110

Leu Cys Leu His Gly Leu Phe Gly Ser Leu Phe Gly Val Thr Pro Asp
        115                 120                 125

Pro Lys Val Ile Glu Glu Ser Glu Ala Lys Leu Val Gln Val Leu Asn
    130                 135                 140

Ile Tyr Glu Glu Arg Leu Ser Lys Thr Lys Tyr Leu Ala Gly Asp Phe
145                 150                 155                 160

Phe Ser Ile Ala Asp Ile Ser His Leu Pro Phe Leu Asp Tyr Val Val
                165                 170                 175

Asn Asn Met Gly Lys Lys Tyr Leu Leu Glu Arg Lys His Val Gly
            180                 185                 190

Ala Trp Trp Asp Asp Ile Ser Ser Arg Pro Ser Trp Asn Lys Val Leu
        195                 200                 205

Gln Leu Tyr Arg Ala Pro Ile
    210                 215
```

<210> SEQ ID NO 43
<211> LENGTH: 1179
<212> TYPE: DNA
<213> ORGANISM: SOYBEAN

<400> SEQUENCE: 43

```
gttcacttca ctttctcagt gcagttgttg cctaatgcaa tggaggaaga agccaaggtg     60
gttttgttgg gtgcacggtt cagtatgttt gagatgagag ttaagatagc tttggcagag    120
```

-continued

```
aaaggaatca aatatgagta catggaacaa gatctcacca acaagagtac tttgcttcaa      180
gaaatgaacc caattcacaa gaagattcca gttctcatac atcatggaag acctatctgt      240
gagtccctca taattgttga gtatattgat atggtttggg acaacaattg tcctttgctt      300
ccctctgatc cctaccacaa agctcaagcc aggttctggg ctgattttgt agatcagaag      360
gtgtatcatg cttctaagag agtttggatt tcaaagggag atgagaaaga ggtggcaaaa      420
aaggacttcc tagagagctt aaagcaattg gaggagtttc ttggagacaa gccttatttt      480
gggggtgaca catttgggtt tgttgatgtt gctcttattc ctttctattg ctggttttat      540
acttatgaga cttttggaaa cttcaaagtg gagggagagt atccaaaact tatctcctgg      600
gccaagagat gcatgcagaa ggaaagtgta tctgaaactc ttgcagatga gagggaggtt      660
tatgaggctg ttttggatta taagaacaaa tttatattga actaagggaa cactgtgaag      720
tgtttgttaa agctgtgaga gtttgcctgt gagatagacc tagtactaca gattctgtta      780
gttattttta tattagttag ctattgtgat cccaataaaa tctcaagtag ttgaggtttt      840
ttttagcaaa tttcaaaatt attataaatt tcaaattggc tctaagtgta taaataggca      900
ttctcattta tgaaatattg ccttctatct tcaattctta tgcctcaatt tttatctcaa      960
gcaagtttca gttttttagt ttctcggcaa gttttagttg gtggtgacaa tttgcattag     1020
acactgaggt gtgtgaactg taagaacaaa accacatggt tctagccttg tcattgccgt     1080
gtacttatat tctttaatgc acattcttat tgtattttca agacttctga ctgaatttcc     1140
attatgaaga tctcttcacg gaaaaaaaaa aaaaaaaaa                            1179
```

<210> SEQ ID NO 44
<211> LENGTH: 221
<212> TYPE: PRT
<213> ORGANISM: SOYBEAN

<400> SEQUENCE: 44

```
Met Glu Glu Glu Ala Lys Val Val Leu Leu Gly Ala Arg Phe Ser Met
  1               5                  10                  15

Phe Glu Met Arg Val Lys Ile Ala Leu Ala Glu Lys Gly Ile Lys Tyr
             20                  25                  30

Glu Tyr Met Glu Gln Asp Leu Thr Asn Lys Ser Thr Leu Leu Gln Glu
         35                  40                  45

Met Asn Pro Ile His Lys Lys Ile Pro Val Leu Ile His His Gly Arg
     50                  55                  60

Pro Ile Cys Glu Ser Leu Ile Ile Val Glu Tyr Ile Asp Met Val Trp
 65                  70                  75                  80

Asp Asn Asn Cys Pro Leu Leu Pro Ser Asp Pro Tyr His Lys Ala Gln
                 85                  90                  95

Ala Arg Phe Trp Ala Asp Phe Val Asp Gln Lys Val Tyr His Ala Ser
            100                 105                 110

Lys Arg Val Trp Ile Ser Lys Gly Asp Glu Lys Glu Val Ala Lys Lys
        115                 120                 125

Asp Phe Leu Glu Ser Leu Lys Gln Leu Glu Glu Phe Leu Gly Asp Lys
    130                 135                 140

Pro Tyr Phe Gly Gly Asp Thr Phe Gly Phe Val Asp Val Ala Leu Ile
145                 150                 155                 160

Pro Phe Tyr Cys Trp Phe Tyr Thr Tyr Glu Thr Phe Gly Asn Phe Lys
                165                 170                 175

Val Glu Gly Glu Tyr Pro Lys Leu Ile Ser Trp Ala Lys Arg Cys Met
            180                 185                 190
```

```
Gln Lys Glu Ser Val Ser Glu Thr Leu Ala Asp Glu Arg Glu Val Tyr
        195                 200                 205
Glu Ala Val Leu Asp Tyr Lys Asn Lys Phe Ile Leu Asn
    210                 215                 220

<210> SEQ ID NO 45
<211> LENGTH: 890
<212> TYPE: DNA
<213> ORGANISM: SOYBEAN

<400> SEQUENCE: 45
tatggtccaa cctatggatc ccccaagagg gtcctggtgt gtctgattga gaaggaaatt      60
gagtttgaaa cagtgcatgt tgatctcttc aagggagaga ataaggaacc tgagttcctt     120
aagctgcagc catttggatc ccttcctgtt attcaagacg gtgattatac tctctatgaa     180
tctcgtgcaa taatcagata cttagctgag aagtataaag accaagggac tgacttattg     240
ggaaagacaa tagaagaaaa gggtctagtg gaacaatggc ttgaagtgga agctcataac     300
tttcacccac cactctacaa cttggttatt aatgttctgt ttgcgccatt aacgggggct     360
ccttcggacc aaaaagtgat agaagaaagt gataaaaaga ttgagaaggt gctggatgtt     420
tatgaggaga ggctgtcaaa gagcaagtac ttggctggtg acttcttcag ccttgctgat     480
cttagccacc tcccatttgg tcactatttg gtgaaccaaa ccgggagagg aaatttggtc     540
agagacagga agcatgtgag tgcttggtgg atgatatta gtaacagacc tgcttggcag     600
aaggttcttc agctatataa ataccctgtc tagttagttc gatctacccc aacattccaa     660
gatggtgtga gggatgtgcc ttcagtgttt tctgatacct gtttgagaat ataatggagg     720
ctatctgcaa gatgtggacc tgtagttttt tttggatttg gatcttttcc tcttcttgaa     780
taataacatt ggatggtgaa aacataaatt taaaattatt gagcagtgtg attagttgtt     840
gagtccatta gttataactt gttatctaag aaaaaaaaaa aaaaaaaaaa                 890

<210> SEQ ID NO 46
<211> LENGTH: 210
<212> TYPE: PRT
<213> ORGANISM: SOYBEAN

<400> SEQUENCE: 46

Tyr Gly Pro Thr Tyr Gly Ser Pro Lys Arg Val Leu Val Cys Leu Ile
  1               5                  10                  15

Glu Lys Glu Ile Glu Phe Glu Thr Val His Val Asp Leu Phe Lys Gly
            20                  25                  30

Glu Asn Lys Glu Pro Glu Phe Leu Lys Leu Gln Pro Phe Gly Ser Leu
        35                  40                  45

Pro Val Ile Gln Asp Gly Asp Tyr Thr Leu Tyr Glu Ser Arg Ala Ile
    50                  55                  60

Ile Arg Tyr Leu Ala Glu Lys Tyr Lys Asp Gln Gly Thr Asp Leu Leu
 65                 70                  75                  80

Gly Lys Thr Ile Glu Glu Lys Gly Leu Val Glu Gln Trp Leu Glu Val
                85                  90                  95

Glu Ala His Asn Phe His Pro Pro Leu Tyr Asn Leu Val Ile Asn Val
            100                 105                 110

Leu Phe Ala Pro Leu Thr Gly Ala Pro Ser Asp Gln Lys Val Ile Glu
        115                 120                 125

Glu Ser Asp Lys Lys Ile Glu Lys Val Leu Asp Val Tyr Glu Glu Arg
    130                 135                 140
```

```
Leu Ser Lys Ser Lys Tyr Leu Ala Gly Asp Phe Phe Ser Leu Ala Asp
145                 150                 155                 160

Leu Ser His Leu Pro Phe Gly His Tyr Leu Val Asn Gln Thr Gly Arg
                165                 170                 175

Gly Asn Leu Val Arg Asp Arg Lys His Val Ser Ala Trp Trp Asp Asp
            180                 185                 190

Ile Ser Asn Arg Pro Ala Trp Gln Lys Val Leu Gln Leu Tyr Lys Tyr
        195                 200                 205

Pro Val
    210

<210> SEQ ID NO 47
<211> LENGTH: 859
<212> TYPE: DNA
<213> ORGANISM: SOYBEAN

<400> SEQUENCE: 47
agaagatgat gggaagtgga gatgtgaagc tgttgagctt ttgggtgagt ccatttggta      60
aaagggttga gtgggctttg aaactgaagg aatagagta tgagtatatt gaagaagata     120
tcttcaacaa gagcaatctc cttctccagt tgaacccggt tcacaagaag gttccggttc     180
ttgttcatgc ccacaaaccg attgcagagt cattcatcat ccttgaatac attgatgaaa     240
catggaagca gtatccattg ttaccttgcc atcctcatca aagagctctt gctcgctttt     300
gggctacttc tgttgaacaa aagcttggga aggctggatg ggtagcaatg tctaccagcg     360
gggaagaaca ggaaaaggct gtgaaggaag ccatagaaat gatggagaaa atagaagaag     420
agattaaggg aaagaaattt tttggaggag acaatattgg gtaccttgac attgctcttg     480
gatggattgc ttacttggtt cctgtttggg aggaagttgg atcaatgcag ataattgacc     540
cattgaaatt tccagccact actgaatgga taaccaattt tctcagccac cctttgatca     600
aggacagttt gcccccaaga gataagatgc ttgtttacta ccacaatcgc aagaacaact     660
tgccttccgt ctttcgtaac ttggtcaagg attagatttg ttcctccatg tgtgtgtgga     720
atcaaattca gtgaagctat ccttttctca cagatgatgt cttaaacaaa ttatgaattg     780
attaaattta ctctagtaac atgtacgtct ttaactgaaa aaaaaaaaaa aaaaaaaaa     840
aaaaaaaaaa aaaaaaaaa                                                 859

<210> SEQ ID NO 48
<211> LENGTH: 229
<212> TYPE: PRT
<213> ORGANISM: SOYBEAN

<400> SEQUENCE: 48

Met Met Gly Ser Gly Asp Val Lys Leu Leu Ser Phe Trp Val Ser Pro
1               5                   10                  15

Phe Gly Lys Arg Val Glu Trp Ala Leu Lys Leu Lys Gly Ile Glu Tyr
                20                  25                  30

Glu Tyr Ile Glu Glu Asp Ile Phe Asn Lys Ser Asn Leu Leu Leu Gln
            35                  40                  45

Leu Asn Pro Val His Lys Lys Val Pro Val Leu Val His Ala His Lys
        50                  55                  60

Pro Ile Ala Glu Ser Phe Ile Ile Leu Glu Tyr Ile Asp Glu Thr Trp
65                  70                  75                  80

Lys Gln Tyr Pro Leu Leu Pro Cys His Pro His Gln Arg Ala Leu Ala
                85                  90                  95
```

```
Arg Phe Trp Ala Thr Ser Val Glu Gln Lys Leu Gly Lys Ala Gly Trp
             100                 105                 110

Val Ala Met Ser Thr Ser Gly Glu Glu Gln Glu Lys Ala Val Lys Glu
         115                 120                 125

Ala Ile Glu Met Met Glu Lys Ile Glu Glu Ile Lys Gly Lys Lys
     130                 135                 140

Phe Phe Gly Gly Asp Asn Ile Gly Tyr Leu Asp Ile Ala Leu Gly Trp
145                 150                 155                 160

Ile Ala Tyr Leu Val Pro Val Trp Glu Val Gly Ser Met Gln Ile
                 165                 170                 175

Ile Asp Pro Leu Lys Phe Pro Ala Thr Thr Glu Trp Ile Thr Asn Phe
             180                 185                 190

Leu Ser His Pro Leu Ile Lys Asp Ser Leu Pro Arg Asp Lys Met
         195                 200                 205

Leu Val Tyr Tyr His Asn Arg Lys Asn Asn Leu Pro Ser Val Phe Arg
     210                 215                 220

Asn Leu Val Lys Asp
225

<210> SEQ ID NO 49
<211> LENGTH: 836
<212> TYPE: DNA
<213> ORGANISM: SOYBEAN

<400> SEQUENCE: 49
gatgtgaaag tacttggatt ttggtcaagc cctttcgttc atagagtgat atgggctcta     60
aagttgaaga acattagtta tgagtacata gaggttgata ggttcaacaa agtgagcta    120
cttcttcaat ccaatccagt ttacaagaaa gtccctgtgc ttattcatgg aggcaaagcc    180
attgcagagt ctcttgtcat tcttgaatac atcgaagaaa cgtggccaga gaaccaccca    240
ttgctgccaa agacaaccca tcaaagggcc ttggctcgct tttggattaa atttggagag    300
gattcgattg cttctattac cgatttgttt cttggaccct ctaaagatga acaagaaaga    360
gcaagtgcaa agaaaaaggc agaagaaact atcatggtaa tggaagagca aggcctagga    420
gacaagaagt tctttggagg caacaatatt ggaatggtgg atatagctca tggatgccta    480
agtcattggt tagaaggctt ggaggaaatt gtggggatga aattgattga gccaaacaaa    540
tttcctcggt tgcatgcgtg gactcaaaat ttcaagcaag ttcctgttat taaagaaaac    600
cttcctgatt atgagaaact gttgatccat cttgaatggc gtaggcaggg atatgttaca    660
tagtagaact agaaatcata aaatgggtaa tgaaattatg actatagtct ataggcctat    720
agtgaatagg agtttagcac attcacatgt gattagtgaa cttaaaaaag tttggtttta    780
tatataaaat aaaataaaaa aaatttggga gagcatttaa aaaaaaaaaa aaaaaa        836

<210> SEQ ID NO 50
<211> LENGTH: 220
<212> TYPE: PRT
<213> ORGANISM: SOYBEAN

<400> SEQUENCE: 50

Asp Val Lys Val Leu Gly Phe Trp Ser Ser Pro Phe Val His Arg Val
  1               5                  10                  15

Ile Trp Ala Leu Lys Leu Lys Asn Ile Ser Tyr Glu Tyr Ile Glu Val
             20                  25                  30

Asp Arg Phe Asn Lys Ser Glu Leu Leu Leu Gln Ser Asn Pro Val Tyr
         35                  40                  45
```

Lys Lys Val Pro Val Leu Ile His Gly Gly Lys Ala Ile Ala Glu Ser
 50                  55                  60

Leu Val Ile Leu Glu Tyr Ile Glu Thr Trp Pro Glu Asn His Pro
 65                  70                  75                  80

Leu Leu Pro Lys Asp Asn His Gln Arg Ala Leu Ala Arg Phe Trp Ile
                 85                  90                  95

Lys Phe Gly Glu Asp Ser Ile Ala Ser Ile Thr Asp Leu Phe Leu Gly
                100                 105                 110

Pro Ser Lys Asp Glu Gln Glu Arg Ala Ser Ala Lys Lys Lys Ala Glu
                115                 120                 125

Glu Thr Ile Met Val Met Glu Glu Gln Gly Leu Gly Asp Lys Lys Phe
130                 135                 140

Phe Gly Gly Asn Asn Ile Gly Met Val Asp Ile Ala His Gly Cys Leu
145                 150                 155                 160

Ser His Trp Leu Glu Gly Leu Glu Glu Ile Val Gly Met Lys Leu Ile
                165                 170                 175

Glu Pro Asn Lys Phe Pro Arg Leu His Ala Trp Thr Gln Asn Phe Lys
                180                 185                 190

Gln Val Pro Val Ile Lys Glu Asn Leu Pro Asp Tyr Glu Lys Leu Leu
                195                 200                 205

Ile His Leu Glu Trp Arg Arg Gln Gly Tyr Val Thr
210                 215                 220

<210> SEQ ID NO 51
<211> LENGTH: 853
<212> TYPE: DNA
<213> ORGANISM: SOYBEAN

<400> SEQUENCE: 51
gtgaagctgt tgagcttttt tgcgagtcca tttggcaaaa gggttgaatg ggcattgaaa     60
ctgaagggtg tggagtatga gtacatagaa caagatatct tcaacaagac tagtctcctt    120
ctccagttga acccggttca caagaaggtt ccggttcttg ttcatgccca caaacccatc    180
gctgagtcat tcgtcatcgt tgaatacgtt gatgaaacat ggaagcagta tccactgttg    240
cctcgagacc cttatcaaag agcacttgct cgattttggg ctaatttcgc tgagcaaaag    300
cttttagatg cagcatggat tggtatgtat agcagcgggg atgagcagca aaacgctgtg    360
aaagtagcca gagaagcaat agagaagata gaagaagaga ttaagggaaa gaaatatttt    420
ggaggggaga atataggata ccttgacatt gcacttggat ggatctctta ctggcttcct    480
atttgggagg aagttggatc gatacagata attgacccat tgaaatttcc agccatcact    540
gcatggatca ccaattttct tagccatcct gtgatcaagg acaacttgcc cccaagagac    600
aagatgcttg tttacttcca cagtcgcaga actgcgcttt cttcaacttt tcagggctga    660
ttcaagtttt aatttggatc tatatgtttc ttatggtcca tgtgatataa taagaatatc    720
agggaatcat actagctaag tctctgtgct attattttct gagattgtgg atttttattta   780 gacttttct tattaggtag agaagtttgt ttggttaagt tttcaataat aaattatgtc    840
ttttttatta aaa                                                       853

<210> SEQ ID NO 52
<211> LENGTH: 219
<212> TYPE: PRT
<213> ORGANISM: SOYBEAN

<400> SEQUENCE: 52

| | | | | | | | | | | | | | | |
|---|---|---|---|---|---|---|---|---|---|---|---|---|---|---|
|Val|Lys|Leu|Leu|Ser|Phe|Phe|Ala|Ser|Pro|Phe|Gly|Lys|Arg|Val|Glu|
|1| | | |5| | | |10| | | |15| | |

Val Lys Leu Leu Ser Phe Phe Ala Ser Pro Phe Gly Lys Arg Val Glu
1               5                   10                  15

Trp Ala Leu Lys Leu Lys Gly Val Glu Tyr Glu Tyr Ile Glu Gln Asp
            20                  25                  30

Ile Phe Asn Lys Thr Ser Leu Leu Leu Gln Leu Asn Pro Val His Lys
        35                  40                  45

Lys Val Pro Val Leu Val His Ala His Lys Pro Ile Ala Glu Ser Phe
    50                  55                  60

Val Ile Val Glu Tyr Val Asp Glu Thr Trp Lys Gln Tyr Pro Leu Leu
65                  70                  75                  80

Pro Arg Asp Pro Tyr Gln Arg Ala Leu Ala Arg Phe Trp Ala Asn Phe
                85                  90                  95

Ala Glu Gln Lys Leu Leu Asp Ala Ala Trp Ile Gly Met Tyr Ser Ser
            100                 105                 110

Gly Asp Glu Gln Gln Asn Ala Val Lys Val Ala Arg Glu Ala Ile Glu
        115                 120                 125

Lys Ile Glu Glu Glu Ile Lys Gly Lys Lys Tyr Phe Gly Gly Glu Asn
130                 135                 140

Ile Gly Tyr Leu Asp Ile Ala Leu Gly Trp Ile Ser Tyr Trp Leu Pro
145                 150                 155                 160

Ile Trp Glu Glu Val Gly Ser Ile Gln Ile Ile Asp Pro Leu Lys Phe
                165                 170                 175

Pro Ala Ile Thr Ala Trp Ile Thr Asn Phe Leu Ser His Pro Val Ile
            180                 185                 190

Lys Asp Asn Leu Pro Pro Arg Asp Lys Met Leu Val Tyr Phe His Ser
        195                 200                 205

Arg Arg Thr Ala Leu Ser Ser Thr Phe Gln Gly
    210                 215

<210> SEQ ID NO 53
<211> LENGTH: 841
<212> TYPE: DNA
<213> ORGANISM: SOYBEAN

<400> SEQUENCE: 53
gaggtgaagc ttcatggatt ttggtatagt ccctacactt tgagggtggt atggaccttaa    60 aagttaaagg ataccata tcaaaacata gaagaagacc gctacaataa gagtcttcaa    120
cttcttgaat acaacccagt atacaagaaa actccagtgc ttgtccataa tggaaaaccc    180
ttatgtgagt ccatgcttat tgttgaatac attgatgaga tttggtcaca taattcatta    240
cttcctgctg atccctacga gagagctctg gcaaggtttt gggttaaata tgctgatgat    300
gacatgtttt ctgcagttat tgcattcttc cttagcaata atgatgaaga gcgagaaaag    360
agcatagaga agatatggga gcatctcagg gttgttgaga atcagtgttt tggtgatcag    420
aagaaatttt tggggggaga cattattaac attatgggaca tagcttttgg gtccatattc    480
aaaattcttg tggttgcaga agatattctt gacgcgaagg tcctggaaga tgagaaattc    540
cctcacttgc attcatggta taataatttc aaggatgttg cagttattaa agaaaacctc    600
ccagaccatg agaaaatggt ggcttttgct aagtttatta gagaaaaacg tttggcatgt    660
acctaagaaa gtaatcttat atgagatcaa gtatgaatca ctttgtatct gtctgaatcg    720
ttttgttatg cgtgtttctt tagtttccac tccattatta ggatgtcttg acatatctgt    780

```
gaaagcaata aaagtttaat gggatgtact ggattagaat tttaaaaaaa aaaaaaaaa     840
a                                                                    841
```

<210> SEQ ID NO 54
<211> LENGTH: 221
<212> TYPE: PRT
<213> ORGANISM: SOYBEAN

<400> SEQUENCE: 54

```
Glu Val Lys Leu His Gly Phe Trp Tyr Ser Pro Tyr Thr Leu Arg Val
  1               5                  10                  15

Val Trp Thr Leu Lys Leu Lys Asp Ile Pro Tyr Gln Asn Ile Glu Glu
                 20                  25                  30

Asp Arg Tyr Asn Lys Ser Leu Gln Leu Leu Glu Tyr Asn Pro Val Tyr
             35                  40                  45

Lys Lys Thr Pro Val Leu Val His Asn Gly Lys Pro Leu Cys Glu Ser
         50                  55                  60

Met Leu Ile Val Glu Tyr Ile Asp Glu Ile Trp Ser His Asn Ser Leu
 65                  70                  75                  80

Leu Pro Ala Asp Pro Tyr Glu Arg Ala Leu Ala Arg Phe Trp Val Lys
                 85                  90                  95

Tyr Ala Asp Asp Met Phe Ser Ala Val Ile Ala Phe Phe Leu Ser
            100                 105                 110

Asn Asn Asp Glu Glu Arg Glu Lys Ser Ile Glu Lys Ile Trp Glu His
        115                 120                 125

Leu Arg Val Val Glu Asn Gln Cys Phe Gly Asp Gln Lys Lys Phe Phe
    130                 135                 140

Gly Gly Asp Ile Ile Asn Ile Met Asp Ile Ala Phe Gly Ser Ile Phe
145                 150                 155                 160

Lys Ile Leu Val Val Ala Glu Asp Ile Leu Asp Ala Lys Val Leu Glu
                165                 170                 175

Asp Glu Lys Phe Pro His Leu His Ser Trp Tyr Asn Asn Phe Lys Asp
            180                 185                 190

Val Ala Val Ile Lys Glu Asn Leu Pro Asp His Glu Lys Met Val Ala
        195                 200                 205

Phe Ala Lys Phe Ile Arg Glu Lys Arg Leu Ala Cys Thr
    210                 215                 220
```

<210> SEQ ID NO 55
<211> LENGTH: 1290
<212> TYPE: DNA
<213> ORGANISM: SOYBEAN

<400> SEQUENCE: 55

```
gttcagaagg cttgatgcac aacagcccca aaaggcgaag ctagttggga taaaaggta     60 atttgaagaa aaagaaaaca gaggcttagg caactaagaa agaaagatga agctgaaggt   120
atatgcggac cgcatgtccc agccatcccg tgcggttctc atattttgca aagtgaatgg   180
aatagatttt gaggagatca agtcgattt atccaaacgt cagcagttat ctcccgaatt    240
ccgagcggtt aacccttaa ggaaagtccc tgctattgtt gatggaaggt tcaagctatt    300
tgagagtcat gctattctca tatatcttgc ttctgcattt ccaggagttg cagaccattg   360
gtacccggct gatcttttcca ggagagcaag aattcactcg gtgttagatt ggcatcacca   420
gaatttgcgt cgtggagcag cttcatttgt tctaaatact gtactagctc cactattggg   480
cctacgagca aaccaacaag cagctgctga agccgagaaa attttgattt catctttgtc   540
```

```
aacaattgag aacatttggc ttaaggggaa tggacagtac ttgcttggtg gcttgcggcc    600
atccatagca gatctcagtc tggtttgtga aattatgcaa ttagagcttt tagatgagaa    660
ggaccgtgat cgtattcttg gccctcacaa gaaggttcag cagtggattg agagcacaag    720
aaatgcaacg aggcctcatt ttgatgaagt tcatacaatc ctctataagc tcaaaacgag    780
gctttctgag cagcaatcta atcaggcaga tggcgtgatg caatctagga ttagaacccc    840
tctaaattca aagatgtgaa caaacaacca tgccagtaac gtgcctgtga caacttatat    900
atgtgtgtgt gtgtgtgttg gctgcaagta tcactgtatc aggtttgaaa catcaaagat    960
gaagtttatg tctgtattga gaccccttaa tctaagtaag ttgggcaggt aataaatgtg   1020
atttccacat gaagatacaa tcgtctcctc ctatgagcag atttggcggc aataatgtta   1080
gtctgtcctt tatatttgcc acgcacaata ttttctagga gctggtaaat tgctgtagta   1140
tagacctatg ttttttttgtt gaacccggat ctccctcgat ccaagagcca atgactaatt   1200
ccccaaggcc atgatttgta caatataaat ttgtatgcat tatccaatgg caatgacgtg   1260
ggaacattat gcaaaaaaaa aaaaaaaaa                                     1290
```

<210> SEQ ID NO 56
<211> LENGTH: 250
<212> TYPE: PRT
<213> ORGANISM: SOYBEAN

<400> SEQUENCE: 56

```
Met Lys Leu Lys Val Tyr Ala Asp Arg Met Ser Gln Pro Ser Arg Ala
 1               5                  10                  15

Val Leu Ile Phe Cys Lys Val Asn Gly Ile Asp Phe Glu Glu Ile Lys
            20                  25                  30

Val Asp Leu Ser Lys Arg Gln Gln Leu Ser Pro Glu Phe Arg Ala Val
        35                  40                  45

Asn Pro Leu Arg Lys Val Pro Ala Ile Val Asp Gly Arg Phe Lys Leu
    50                  55                  60

Phe Glu Ser His Ala Ile Leu Ile Tyr Leu Ala Ser Ala Phe Pro Gly
65                  70                  75                  80

Val Ala Asp His Trp Tyr Pro Ala Asp Leu Ser Arg Arg Ala Arg Ile
                85                  90                  95

His Ser Val Leu Asp Trp His His Gln Asn Leu Arg Arg Gly Ala Ala
           100                 105                 110

Ser Phe Val Leu Asn Thr Val Leu Ala Pro Leu Gly Leu Arg Ala
       115                 120                 125

Asn Gln Gln Ala Ala Ala Glu Ala Glu Lys Ile Leu Ile Ser Ser Leu
   130                 135                 140

Ser Thr Ile Glu Asn Ile Trp Leu Lys Gly Asn Gly Gln Tyr Leu Leu
145                 150                 155                 160

Gly Gly Leu Arg Pro Ser Ile Ala Asp Leu Ser Leu Val Cys Glu Ile
               165                 170                 175

Met Gln Leu Glu Leu Leu Asp Glu Lys Asp Arg Asp Arg Ile Leu Gly
           180                 185                 190

Pro His Lys Lys Val Gln Gln Trp Ile Glu Ser Thr Arg Asn Ala Thr
       195                 200                 205

Arg Pro His Phe Asp Glu Val His Thr Ile Leu Tyr Lys Leu Lys Thr
   210                 215                 220

Arg Leu Ser Glu Gln Gln Ser Asn Gln Ala Asp Gly Val Met Gln Ser
225                 230                 235                 240
```

```
Arg Ile Arg Thr Pro Leu Asn Ser Lys Met
                245                 250
```

SOYBEAN GLUTATHIONE-S-TRANSFERASE ENZYMES

This is a continuation-in-part of Application Ser. No. 08/924,747 filed Sep. 5, 1997, now pending.

FIELD OF THE INVENTION

This invention is in the field of plant molecular biology. More specifically, this invention pertains to nucleic acid fragments encoding soybean glutathione-S-transferase (GST) enzymes involved in the detoxification of xenobiotic compounds in plants and seeds.

BACKGROUND OF THE INVENTION

Glutathione-S-transferases (GST) are a family of enzymes which catalyze the conjugation of glutathione, homoglutathione (hGSH) and other glutathione-like analogs via a sulfhydryl group, to a large range of hydrophobic, electrophilic compounds. The conjugation can result in detoxification of these compounds. GST enzymes have been identified in a range of plants including maize (Wosnick et al., *Gene* (Amst) 76 (1) (1989) 153–160; Rossini et al., *Plant Physiology* (Rockville) 112 (4) (1996) 1595–1600; Holt et al., *Planta* (Heidelberg) 196 (2) (1995) 295–302), wheat (Edwards et al., *Pestic. Biochem. Physiol.* (1996) 54(2), 96–104), sorghum (Hatzios et al., *J. Environ. Sci. Health,* Part B (1996), B31(3), 545–553), arabidopsis (Van Der Kop et al., *Plant Molecular Biology* 30 (4) (1996), sugarcane (Singhal et al., *Phytochemistry* (OXF) 30 (5) (1991) 1409–1414), soybean (Flury et al., *Physiologia Plantarum* 94 (1995) 594–604) and peas (Edwards R., *Physiologia Plantarum* 98 (3) (1996) 594–604). GST's can comprise a significant portion of total plant protein, for example attaining from 1 to 2% of the total soluble protein in etiolated maize seedlings (Timmermann, *Physiol. Plant.* (1989) 77(3), 465–71).

Glutathione S-transferases (GSTs; EC 2.5.1.18) catalyze the nucleophilic attack of the thiol group of GSH to various electrophilic substrates. Their functions and regulation in plants has been recently reviewed (Marrs et al., *Annu Rev Plant Physiol Plant Mol Biol* 47:127–58 (1996); Droog, F. *J Plant Growth Regul* 16:95–107, (1997)). They are present at every stage of plant development from early embryogenesis to senescence and in every tissue type examined. The agents that have been shown to cause an increase in GST levels have the potential to cause oxidative destruction in plants, suggesting a role for GSTs in the protection from oxidative damage. In addition to their role in the protection from oxidative damage, GSTs have the ability to nonenzymatically bind certain small molecules, such as auxin (Zettl, et al., *PNAS* 91: 689–693, (1994)) and perhaps regulate their bioavailability. Furthermore the addition of GSH to a molecule serves as an "address" to send that molecule to the plant vacuole (Marrs, et al., *Nature* 375: 397–400, (1995)).

GSTs have also been implicated in the detoxification of certain herbicides. Maize GSTs have been well characterized in relation to herbicide metabolism. Three genes from maize have been cloned: GST 29 (Shah et al., *Plant Mol Biol* 6, 203–211(1986)), GST 27 (Jepson et al., *Plant Mol Biol* 26:1855–1866, (1994)), GST 26 (Moore et al., *Nucleic Acids Res* 14:7227–7235 (1986)). These gene products form four GST isoforms: GST I (a homodimer of GST 29), GST IV (a heterodimer of GST 29 and GST 27), GST III (a homodimer of GST 26), and GST IV (a homodimer of GST 27). GST 27 is highly inducible by safener compounds (Jepson (1994) supra; Holt et al., *Planta* 196:295–302, (1995)) and over-expression of GST 27 in tobacco confers alachlor resistance to transgenic tobacco (Jepson, personal communication). Additionally Bridges et al. (U.S. Pat. No. 5,589,614) disclose the sequence of a maize derived GST isoform II promoter useful for the expression of foreign genes in maize and wheat. In soybean, herbicide compounds conjugated to hGSH have been detected and correlated with herbicide selectivity (Frear et al., *Physiol* 20: 299–310 (1983); Brown et al., *Pest Biochem Physiol* 29:112–120, (1987)). This implies that hGSH conjugation is an important determinant in soybean herbicide selectivity although this hypothesis has not been characterized on a molecular level.

Glutathione (the tripeptide γ-glu-cys-gly, or GSH) is present in most plants and animals. However, in some plants from the family Leguminaceae the major free thiol is homoglutathione. For example, soybeans (*Glycine max*) have nearly undetectable levels of glutathione with the tripeptide homoglutathione (γ-glu-cys-β-ala) apparently substituting for the same functions. Some herbicides are detoxified in soybeans by homoglutathione conjugation catalyzed by glutathione S-transferase (GST) enzyme(s).

Homoglutathione (hGSH) was originally detected in Phaseolus vulgaris and several other leguminous species (Price, C. A., *Nature* 180: 148–149, (1957)). The structure of hGSH (Carnegie, P. R., *Biochemical Journal* 89:471–478 (1963)) was determined to be the tripeptide γ-glu-cys-β-ala. Homoglutathione has not been found in non-leguminous species. In plants from the family Legumaceae, the ratio of hGSH to GSH varies according to both species and tissue examined. In seeds and leaves of the tribe Vicieae, only traces of hGSH were found in addition to the main thiol GSH, whereas in roots the hGSH content exceeded the GSH content. The tribe Trifolieae contained both tripeptides and in the tribe Phaseoleae, hGSH predominated. In soybean (*Glycine max*), a member of the Phaseoleae, hGSH constitutes 99% of the free thiol in leaves and seeds and greater than 95% of the free thiol in soybean roots (Klapheck, S., *Physiolgia Plantarum* 74: 727–732 (1988)). As such, it is essential that soybean glutathione S-transferases be able to efficiently utilize hGSH.

Some efforts have been made to alter plant phenotypes by the expression of either plant or mammalian foreign GST genes or their promoters in mature plant tissue. For example, Helmer et al. (U.S. Pat. No. 5,073,677) teach the expression of a rat GST gene in tobacco under the control of a strong plant promoter. Similarly, Jepson et al. (WO 97/11189) disclose a chemically inducible maize GST promoter useful for the expression of foreign proteins in plants; Chilton et al. (EP 256223) discuss the construction of herbicide tolerant plants expressing a foreign plant GST gene; and Bieseler et al. (WO 96/23072) teach DNA encoding GSTIIIc, its recombinant production and transgenic plants containing the DNA having a herbicide-tolerant phenotype.

Manipulation of nucleic acid fragments encoding soybean GST to use in screening in assays, the creation of herbicide-tolerant transgenic plants, and altered production of GST enzymes depend on the heretofore unrealized isolation of nucleic acid fragments that encode all or a substantial portion of a soybean GST enzyme.

SUMMARY OF THE INVENTION

The present invention provides nucleic acid fragments isolated from soybean encoding all or a substantial portion of a GST enzyme. The isolated nucleic acid fragment is selected from the group consisting of (a) an isolated nucleic acid fragment encoding all or a substantial portion of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, and SEQ ID NO:56; (b) an isolated nucleic acid fragment that is substantially similar to an isolated nucleic acid fragment encoding all or a substantial portion of the amino acid sequence sequence selected from the group consisting of SEQ ID NO:2, SEQ ID NO:4, SEQ ID NO:6, SEQ ID NO:8, SEQ ID NO: 10, SEQ ID NO: 12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, and SEQ ID NO:56; and (c) an isolated nucleic acid fragment that is complementary to (a) or (b). The nucleic acid fragments and corresponding polypeptides are contained in the accompanying Sequence Listing and described in the Brief Description of the Invention.

In another embodiment, the instant invention relates to chimeric genes encoding soybean GST enzymes or to chimeric genes that comprise nucleic acid fragments as described above, the chimeric genes operably linked to suitable regulatory sequences, wherein expression of the chimeric genes results in altered levels of the encoded enzymes in transformed host cells.

The present invention further provides a transformed host cell comprising the above described chimeric gene. The transformed host cells can be of eukaryotic or prokaryotic origin. The invention also includes transformed plants that arise from transformed host cells of higher plants, and from seeds derived from such transformed plants, and subsequent progeny.

Additionally, the invention provides methods of altering the level of expression of a soybean GST enzyme in a host cell comprising the steps of; (i) transforming a host cell with the above described chimeric gene and; (ii) growing the transformed host cell produced in step (i) under conditions that are suitable for expression of the chimeric gene wherein expression of the chimeric gene results in production of altered levels of a plant GST enzyme in the transformed host cell relative to expression levels of an untransformed host cell.

In an alternate embodiment, the present invention provides methods of obtaining a nucleic acid fragment encoding all or substantially all of the amino acid sequence encoding a soybean GST enzyme comprising either hybridization or primer-directed amplification methods known in the art and using the above described nucleic acid fragment. A primer-amplification-based method uses SEQ ID NOS.:1, 3, 5, 7, 9, 11, 13, 15, 17, 19, 21, 23, 25, 27, 33, 35, 37, 39, 41, 43, 45, 47, 49, 51, 53, and 55. The product of these methods is also part of the invention.

Another embodiment of the invention includes a method for identifying a compound that inhibits the activity of a soybean GST enzyme encoded by the nucleic acid fragment and substantially similar and complementary nucleic acid fragments of SEQ ID NOS.:1, 3, 5, 7, 9, 11, 13, 15, 17, 19, 21, 23, 25, 27, 33, 35, 37, 39, 41, 43, 45, 47, 49, 51, 53, and 55. The method has the steps: (a) transforming a host cell with the above described chimeric gene; (b) growing the transformed host cell under conditions that are suitable for expression of the chimeric gene wherein expression of the chimeric gene results in production of the GST enzyme; (c) optionally purifying the GST enzyme expressed by the transformed host cell; (d) contacting the GST enzyme with a chemical compound of interest; and (e) identifying the chemical compound of interest that reduces the activity of the soybean GST enzyme relative to the activity of the soybean GST enzyme in the absence of the chemical compound of interest.

This method may further include conducting step (d) in the presence of at least one electrophilic substrate and at least one thiol donor. The isolated nucleic acid fragments of this method are chosen from the group represented by SEQ ID NOS.:1, 3, 5, 7, 9, 11, 13, 15, 17, 19, 21, 23, 25, 27, 33, 35, 37, 39, 41, 43, 45, 47, 49, 51, 53, and 55, and the soybean GST enzyme is selected from the group consisting of SEQ ID NOS.:2, 4, 6, 8, 10, 12, 14, 16, 18, 20, 22, 24, 26, 28, 34, 36, 38, 40, 42, 44, 46, 48, 50, 52, 54, and 56.

The invention further provides a method for identifying a chemical compound that inhibits the activity of the soybean GST enzyme as described herein, wherein the identification is based on a comparison of the phenotype of a plant transformed with the above described chimeric gene contacted with the inhibitor candidate with the phenotype of a transformed plant that is not contacted with the inhibitor candidate. The isolated nucleic acid fragment of this method is selected from the group consisting of SEQ ID NOS.:1, 3, 5, 7, 9, 11, 13, 15, 17, 19, 21, 23, 25, 27, 33, 35, 37, 39, 41, 43, 45, 47, 49, 51, 53, and 55 and the soybean GST enzyme is selected from the group consisting of SEQ ID NOS.:2, 4, 6, 8, 10, 12, 14, 16, 18, 20, 22, 24, 26, 28, 34, 36, 38, 40, 42, 44, 46, 48, 50, 52, 54, 20 and 56.

In another embodiment, the invention provides a method for identifying a substrate for the soybean GST enzyme. The method comprises the steps of: (a) transforming a host cell with a chimeric gene comprising the nucleic acid fragment as described herein, the chimeric gene encoding a soybean GST enzyme operably linked to at least one suitable regulatory sequence; (b) growing the transformed host cell of step (a) under conditions that are suitable for expression of the chimeric gene resulting in production of the GST enzyme; (c) optionally purifying the GST enzyme expressed by the transformed host cell; (d) contacting the GST enzyme with a substrate candidate; and (e) comparing the activity of soybean GST enzyme with the activity of soybean GST enzyme that has been contacted with the substrate candidate and selecting substrate candidates that increase the activity of the sobyean GST enzyme relative to the activity of soybean GST enzyme in the absence of the substrate candidate. More preferably, step (d) of this method is carried out in the presence of at least one thiol donor. The isolated nucleic acid fragment of this method is selected from the group consisting of SEQ ID NOS.:1, 3, 5, 7, 9, 11, 13, 15, 17, 19, 21, 23, 25, 27, 33, 35, 37, 39, 41, 43, 45, 47, 49, 51, 53, and 55, and the soybean GST enzyme is selected from the group consisting of SEQ ID NOS.:2, 4, 6, 8, 10, 12, 14, 16, 18, 20, 22, 24, 26, 28, 34, 36, 38, 40, 42, 44, 46, 48, 50, 52, 54, and 56.

Alternatively, methods are provided for identifying a soybean GST substrate candidate wherein the identification of the substrate candidate is based on a comparison of the phenotype of a host cell transformed with a chimeric gene expressing a soybean GST enzyme and contacted with a substrate candidate with the phenotype of a similarly transformed host cell grown without contact with a substrate candidate.

The isolated nucleic acid fragment of this method is selected from the group consisting of SEQ ID NOS.:1, 3, 5, 7, 9, 11, 13, 15, 17, 19, 21, 23, 25, 27, 33, 35, 37, 39, 41, 43, 45, 47, 49, 51, 53, and 55, and the soybean GST enzyme is selected from the group consisting of SEQ ID NOS.:2, 4, 6, 8, 10, 12, 14, 16, 18, 20, 22, 24, 26, 28, 34, 36, 38, 40, 42, 44, 46, 48, 50, 52, 54, and 56.

BRIEF DESCRIPTION OF SEQUENCE DESCRIPTIONS AND BIOLOGICAL DEPOSITS

The invention can be more fully understood from the following detailed description and the accompanying sequence descriptions and biological deposits which form a part of this application.

The following sequence descriptions and sequences listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference.

SEQ ID NO:1 is the nucleotide sequence comprising the cDNA insert in clone se1.27b04 encoding a soybean type I GST.

SEQ ID NO:2 is the deduced amino acid sequence of the nucleotide sequence comprising the cDNA insert in clone se1.27b04.

SEQ ID NO:3 is the nucleotide sequence comprising the cDNA insert in clone ssm.pk0026.g11 encoding a soybean type II GST.

SEQ ID NO:4 is the deduced amino acid sequence of the nucleotide sequence comprising the cDNA insert in clone ssm.pk0026.g11.

SEQ ID NO:5 is the nucleotide sequence comprising the cDNA insert in clone GSTa encoding a soybean type III GST.

SEQ ID NO:6 is the deduced amino acid sequence of the nucleotide sequence comprising the cDNA insert in clone GSTa.

SEQ ID NO:7 is the nucleotide sequence comprising the cDNA insert in clone se3.03b09 encoding a soybean type III GST.

SEQ ID NO:8 is the deduced amino acid sequence of the nucleotide sequence comprising the cDNA insert in clone se3.03b09.

SEQ ID NO:9 is the nucleotide sequence comprising the cDNA insert in clone se6.pk0037.h4 encoding a soybean type III GST.

SEQ ID NO: 10 is the deduced amino acid sequence of the nucleotide sequence comprising the cDNA insert in clone se6.pk0037.h4.

SEQ ID NO: 11 is the nucleotide sequence comprising the cDNA insert in clone se6.pk0048.d7 encoding a soybean type m GST.

SEQ ID NO: 12 is the deduced amino acid sequence of the nucleotide sequence comprising the cDNA insert in clone se6.pk0048.d7.

SEQ ID NO: 13 is the nucleotide sequence comprising the cDNA insert in clone ses8w.pk0028.c6 encoding a soybean type III GST.

SEQ ID NO:14 is the deduced amino acid sequence of the nucleotide sequence comprising the cDNA insert in clone ses8w.pk0028.c6.

SEQ ID NO:15 is the nucleotide sequence comprising the cDNA insert in clone sr1.pk0011..d6 encoding a soybean type III GST.

SEQ ID NO:16 is the deduced amino acid sequence of the nucleotide sequence comprising the cDNA insert in clone sr1.pk0011.d6.

SEQ ID NO: 17 is the nucleotide sequence comprising the cDNA insert in clone ss1.pk0002.f7 encoding a soybean type III GST.

SEQ ID NO:18 is the deduced amino acid sequence of the nucleotide sequence comprising the cDNA insert in clone ss1.pk0002.f7.

SEQ ID NO:19 is the nucleotide sequence comprising the cDNA insert in clone ss1.pk0005.e6 encoding a soybean type III GST.

SEQ ID NO:20 is the deduced amino acid sequence of the nucleotide sequence comprising the cDNA insert in clone ss1.pk0005.e6.

SEQ ID NO:21 is the nucleotide sequence comprising the cDNA insert in clone ss1.pk0014.a1 encoding a soybean type III GST.

SEQ ID NO:22 is the deduced amino acid sequence of the nucleotide sequence comprising the cDNA insert in clone ss1.pk0014.a1.

SEQ ID NO:23 is the nucleotide sequence comprising the cDNA insert in clone ss1.pk0020.b10 encoding a soybean type III GST.

SEQ ID NO:24 is the deduced amino acid sequence of the nucleotide sequence comprising the cDNA insert in clone ss1.pk0020.b10.

SEQ ID NO:25 is the nucleotide sequence comprising the cDNA insert in clone ssm.pk0067.g5 encoding a soybean type III GST.

SEQ ID :26 is the deduced amino acid sequence of the nucleotide sequence comprising the cDNA insert in clone ssm.pk0067.g5.

SEQ ID NO:27 is the nucleotide sequence comprising the cDNA insert in lone se1.pk0017.f5 encoding a soybean type IV GST.

SEQ ID NO:28 is the deduced amino acid sequence of the nucleotide sequence comprising the cDNA insert in clone se1.pk0017.f5.

SEQ ID NO:29–32 correspond to primers used in the cloning of GSTa.

SEQ ID NO:33 is the nucleotide sequence comprising the cDNA insert in src3c.pk026.e6 encoding a soybean type III GST.

SEQ ID NO:34 is the deduced amino acid sequence of the nucleotide sequence comprising the cDNA insert in clone src3c.pk026.e6.

SEQ ID NO:35 is the nucleotide sequence comprising the cDNA insert in sls1c.pk007.j17 encoding a soybean type III GST.

SEQ ID NO:36 is the deduced amino acid sequence of the nucleotide sequence comprising the cDNA insert in clone sls1c.pk007.j17.

SEQ ID NO:37 is the nucleotide sequence comprising the cDNA insert in sls2c.pk002.d9 encoding a soybean type III GST.

SEQ ID NO:38 is the deduced amino acid sequence of the nucleotide sequence comprising the cDNA insert in clone sls2c.pk002.d9.

SEQ ID NO:39 is the nucleotide sequence comprising the cDNA insert in sls1c.pk003.f24 encoding a soybean type I GST.

SEQ ID NO:40 is the deduced amino acid sequence of the nucleotide sequence comprising the cDNA insert in clone sls1c.pk003.f24.

SEQ ID NO:41 is the nucleotide sequence comprising the cDNA insert in sdp2c.pk002.l16 encoding a soybean type I GST.

SEQ ID NO:42 is the deduced amino acid sequence of the nucleotide sequence comprising the cDNA insert in clone sdp2c.pk002.l16.

SEQ ID NO:43 is the nucleotide sequence comprising the cDNA insert in sfl1.pk127.07 encoding a soybean type III GST.

SEQ ID NO:44 is the deduced amino acid sequence of the nucleotide sequence comprising the cDNA insert in clone sfl1.pk127.07.

SEQ ID NO:45 is the nucleotide sequence comprising the cDNA insert in sfl1.pk126.i6 encoding a soybean type I GST.

SEQ ID NO:46 is the deduced amino acid sequence of the nucleotide sequence comprising the cDNA insert in clone sfl1.pk126.i6.

SEQ ID NO:47 is the nucleotide sequence comprising the cDNA insert in srr3c.pk001.a17 encoding a soybean type III GST.

SEQ ID NO:48 is the deduced amino acid sequence of the nucleotide sequence comprising the cDNA insert in clone srr3c.pk001.a17.

SEQ ID NO:49 is the nucleotide sequence comprising the cDNA insert in sgs1c.pk001.c16 encoding a soybean type III GST.

SEQ ID NO:50 is the deduced amino acid sequence of the nucleotide sequence comprising the cDNA insert in clone sgs1c.pk001.c16.

SEQ ID NO:51 is the nucleotide sequence comprising the cDNA insert in sl2.pk0010.e2 encoding a soybean type III GST.

SEQ ID NO:52 is the deduced amino acid sequence of the nucleotide sequence comprising the cDNA insert in clone sl2.pk0010.e2.

SEQ ID NO:53 is the nucleotide sequence comprising the cDNA insert in sgs2c.pk001.n19 encoding a soybean type III GST.

SEQ ID NO:54 is the deduced amino acid sequence of the nucleotide sequence comprising the cDNA insert in clone sgs2c.pk001.n19.

SEQ ID NO:55 is the nucleotide sequence comprising the cDNA insert in sde4c.pk002.d4 encoding a soybean type I GST.

SEQ ID NO:56 is the deduced amino acid sequence of the nucleotide sequence comprising the cDNA insert in clone sde4c.pk002.d4.

The transformed *E. coli* sr1.pk0011.d6/pET30(LIC)BL21 (DE3) comprising the *E. coli* host BL21 (DE3), containing the gene sr1.pk001.d6 in a pET30(LIC) vector encoding a soybean type III GST was deposited on Aug. 21, 1997 with the American Type Culture Collection (ATCC), 10801 University Boulevard, Manassas, Va. 20110-2209 U.S.A. under the terms of the Budapest Treaty on the International Recognition of the Deposit of Micro-organisms for the Purpose of Patent Procedure. The deposit is designated as ATCC 98512.

DETAILED DESCRIPTION OF THE INVENTION

The present invention provides novel GST nucleotide sequences and encoded proteins isolated from soybean. GST enzymes are known to function in the process of detoxification of a variety of xenobiotic compounds in plants, most notably, herbicides. Nucleic acid fragments encoding at least a portion of several soybean GST enzymes have been isolated and identified by comparison of random plant cDNA sequences to public databases containing nucleotide and protein sequences using the BLAST algorithms well known to those skilled in the art. The sequences of the present invention are useful in the construction of herbicide-tolerant transgenic plants, in the recombinant production of GST enzymes, in the development of screening assays to identify compounds inhibitory to the GST enzymes, and in screening assays to identify chemical substrates of the GSTs.

In the context of this disclosure, a number of terms shall be utilized. "Glutathione S-Transferase" or "GST" refers to any plant-derived glutathione S-transferase (GST) enzyme capable of catalyzing the conjugation of glutathione, homo-glutathione and other glutathione-like analogs via a sulfhydryl group to hydrophobic and electrophilic compounds. The term "GST" includes amino acid sequences longer or shorter than the length of natural GSTs, such as functional hybrid or partial fragments of GSTs, or their analogues. "GST" is not intended to be limited in scope on the basis of enzyme activity and may encompass amino acid sequences that possess no measurable enzyme activity but are substantially similar to those sequences known in the art to possess the above-mentioned glutathione conjugating activity.

The term "class" or "GST class" refers to a grouping of the various GST enzymes according to amino acid identity. Currently, four classes have been identified and are referred to as "GST class I" "GST class II", "GST class III" and "GST class IV". The grouping of plant GSTs into three classes is described by Droog et al. (*Plant Physiology* 107:1139–1146 (1995)). All available amino acid sequences were aligned using the Wisconsin Genetics Computer Group package (Wisconsin Package Version 9.0, Genetics Computer Group (GCG), Madison, Wis.), and graphically represented on a phylogenetic tree. Three groups were identified: class one including the archetypical sequences from maize GST I (X06755) and GST III (X04375); class two including the archetypical sequence from *Dianthus caryophyllus* (M64628); and class three including the archetypical sequence soybean GH2/4 (M20363). Recently, Applicants have established a further subgroup of the plant GSTs known as class IV GSTs with its archetypical sequence being In2-1 (X58573).

As used herein, an "isolated nucleic acid fragment" is a polymer of RNA or DNA that is single- or double-stranded, optionally contaning synthetic, non-natural or altered nucleotide bases. An isolated nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases result in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less that the entire coding region of a gene, and by nucleic acid fragments that do not share 100% identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C.), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the identical to the DNA sequence of the nucleic acid fragments reported herein. Most preferred are nucleic acid fragments that are at least 95% identical to the DNA sequence of the nucleic acid fragments reported herein.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual,* Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a $T_m$ of 55°, can be used, e.g., 5X SSC, 0.1% SDS, 0.25% milk, and no formamide; or 30% formamide, 5X SSC, 0.5% SDS. Moderate stringency hybridization conditions correspond to a higher $T_m$, e.g., 40% formamide, with 5X or 6X SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (basic Local Alignment Search Tool; Altschul, S. F., et al., (1993) *J. MoL Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular fungal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology (Lesk, A. M., ed.) Oxford*

University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG Pileup program found in the GCG program package, as used in the instant invention, using the Needleman and Wunsch algorithm with their standard default values of gap creation penalty=12 and gap extension penalty=4 (Devereux et al., *Nucleic Acids Res.* 12:387–395 (1984)), BLASTP, BLASTN, and PASTA Pearson et al., *Proc. Natl. Acad. Sci. U.S.A.* 85:2444–2448 (1988). The BLAST X program is publicly available from NCBI and other sources (*BLAST Manual*, Altschul et al., Natl. Cent. Biotechnol. Inf., Natl. Library Med. (NCBI NLM) NIH, Bethesda, Md. 20894; Altschul et al., *J. Mol. Biol.* 215:403–410 (1990)). Another preferred method to determine percent identity, is by the method of DNASTAR protein alignment protocol using the Jotun-Hein algorithm (Hein et al., *Methods Enymol* 183:626–645 (1990)). Default parameters for the Jotun-Hein method for alignments are: for multiple alignments, gap penalty=11, gap length penalty=3; for pairwise alignments ktuple=6. As an illustration, by a polynucleotide having a nucleotide sequence having at least, for example, 95% "identity" to a reference nucleotide sequence of SEQ ID NO:1 it is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the GST enzymes as set forth in SEQ ID Nos: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, and SEQ ID NO:56. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer.

Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okarnuro and Goldberg, (1989) *Biochemistry of Plants* 15:1–82. It is further recognized that since in most cases the exact boundaries of regulatory sequences have not been completely defmed, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to MRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. ((1989) *Plant Cell* 1:671–680).

"RNA script" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or MRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth Enzymol.* 143:277) and particle-accelerated or "gene gun" transformation technology (Klein et al. (1987) *Nature* (London) 327:70–73; U.S. Pat. No. 4,945,050).

The term "herbicide-tolerant plant" as used herein is defined as a plant that survives and preferably grows normally at a usually effective dose of a herbicide. Herbicide tolerance in plants according to the present invention refers to detoxification mechanisms in a plant, although the herbicide binding or target site is still sensitive.

"Thol donor" refers to a compound that contains the structure RSH (where R is not equal to H). Within the context of the present invention suitable thiol donors may include, but are not limited to, Glutathione and homoglutathione.

"Electrophilic substrate" refers to a compound that is amenable to conjugation with glutathione or homoglutathione via a sulfhydryl group. Electrophilic substrates include a wide variety of compounds including pesticides, anti-pathogenic compounds such as fungicides and profungicides, pheramones, and herbicides. Within the context of the present invention electrophilic substrates with herbicidal activity may include, but are not limited to, chlorimuronethyl, alachlor, and atrazine, 1-chloro-2,4-dinitrobenzene (CDNB), ethacrynic acid, t-stilbene oxide, and 1,2-epoxy-3-(p-nitrophenoxy)propane.

Standard recombinant DNA and molecular cloning techniques used herein are well known in the art and are described more filly in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Maniatis").

The nucleic acid fragments of the instant invention may be used to isolate cDNAs and genes encoding homologous enzymes from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other GST enzymes, either as cDNAs or genomic DNAs, could be isolated directly by using all or a portion of the instant nucleic acid fragments as DNA hybridization probes to screen libraries from any desired plant using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or fill-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate fill-length cDNAs (Frohman, M. A. and Martin, G. R., (1989) *Techniques* 1:165).

Availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragents of the instant invention may be used to create transgenic plants in which the disclosed GST enzymes are present at higher or lower levels than normal or in cell types or developmental stages in which they are not normally found. This would have the effect of altering the level of GST enzyme available as well as the herbicide-tolerant phenotype of the plant.

Overexpression of the GST enzymes of the instant invention may be accomplished by first constructing chimeric genes in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a GST coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with the genetic sequence for GST, should be capable of promoting expression of the GST such that the transformed plant is tolerant to an herbicide due to the presence of, or increased levels of, GST enzymatic activity. High level plant promoters that may be used in this invention include the promoter of the small subunit (ss) of the ribulose-1,5-bisphosphate carboxylase from example from soybean (Berry-Lowe et al., *J. Molecular and App. Gen.*, 1:483–498 1982)), and the promoter of the chlorophyll a/b binding protein. These two promoters are known to be light-induced in plant cells (See, for example, *Genetic Engineering of Plants, an Agricultural Perspective,* A. Cashmore, Plenum, N.Y. (1983), pages 29–38; Coruzzi, G. et al., *The Journal of Biological Chemistry,* 258:1399 (1983), and Dunsmuir, P. et al., *Journal of Molecular and Applied Genetics,* 2:285 (1983)).

Plasmid vectors comprising the instant chimeric genes can then constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA blots (Southern, *J. Mol. Biol.* 98, 503, (1975)). Northern analysis of mRNA expression (Kroczek, *J. Chromatogr. Biomed Appl,* 618 (1–2) (1993) 133–145), Western analysis of protein expression, or phenotypic analysis.

For some applications it will be useful to direct the instant GST enzymes to different cellular compartments or to facilitate enzyme secretion from a recombinant host cell. It is thus envisioned that the chimeric genes described above may be further supplemented by altering the coding sequences to encode enzymes with appropriate intracellular targeting sequences such as transit sequences (Keegstra, K., *Cell* 56:247–253 (1989)), signal sequences or sequences encoding endoplasmic reticulum localization (Chrispeels, J. J., *Ann. Rev. Plant Phys. Plant Mol Biol.* 42:21–53 (1991)), or nuclear loclization signals (Raikhel, N. *Plant Phys.* 100:1627–1632 (1992)) added and/or with targeting sequences that are already present removed. While the references cited give examples of each of these, the list is not exhaustive and more targeting signals of utility may be discovered in the future that are useful in the invention.

It may also be desirable to reduce or eliminate expression of the genes encoding the instant GST enzymes in plants. In order to accomplish this, chimeric genes designed for co-suppression of the instant GST enzymes can be constructed by linking the genes or gene fragments encoding the enzymes to plant promoter sequences. Alternatively, chimeric genes designed to express antisense RNA for all or part of the instant nucleic acid fragments can be constructed by linking the genes or gene fragment in reverse orientation to plant promoter sequences. Either the co-suppression or antisense chimeric genes could be introduced into plants via transformation wherein expression of the corresponding endogenous genes are reduced or eliminated.

Plants transformed with the present GST genes will have a variety of phenotypes corresponding to the various properties conveyed by the GST class of proteins. Glutathione conjugation catalyzed by GSTs are known to result in sequestration and detoxification of a number of herbicides and other xenobiotics (Marrs et al., *Annu. Rev. Plant Physiol Plant Mol. Biol* 47:127–58 (1996)) and thus will be expected to produce transgenic plants with this phenotype. Other GST proteins are known to be induced by various environmental stresses such as salt stress (Roxas, et al., *Stress tolerance in transgenic seedlings that overexpress glutathione S-transferase,* Annual Meeting of the American Society of Plant Physiologists, (August 1997), abstract 1574, Final Program, Plant Biology and Supplement to Plant Physiology, 301), exposure to ozone (Sharma et al., *Plant Physiology,* 105 (4) (1994) 1089–1096), and exposure to industrial pollutants such as sulfir dioxide (Navari-lzzo et al., *Plant Science* 96 (1–2) (1994) 31–40). It is contemplated that transgenic plants, tolerant to a wide variety of stresses, may be produced by the present method by expressing foreign GST genes in suitable plant hosts.

The instant GST enzymes produced in heterologous host cells, particularly in the cells of microbial hosts, can be used to prepare antibodies to the enzymes by ethods well known to those skilled in the art. The antibodies are useful for detecting the enzymes in situ in cells or in vitro in cell extracts. Preferred heterologous host cells for production of the instant GST enzymes are microbial hosts. Microbial expression systems and expression vectors containing regulatory sequences that direct high level expression of foreign proteins are well known to those skilled in the art. Any of these could be used to construct chimeric genes for production of the instant GST enzymes. These chimeric genes could then be introduced into appropriate microorganisms via transformation to provide high level expression of the enzymes.

Vectors or cassettes usefull for the transformation of suitable host cells are well known in the art. Typically, the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the genes encoding the GST enzymes in the desired host cell, are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, trp, $\lambda P_L$, $\lambda P_R$, T7, tac, and trc (useful for expression in *E. coli*).

Termination control regions may also be derived from various genes native to the preferred hosts. Optionally, a termination site may be unnecessary, however, it is most preferred if included.

An example of a vector for high level expression of the instant GST enzymes in a bacterial host is provided (Example 5).

Additionally, the instant soybean GST enzymes can be used as a targets to facilitate design and/or identification of inhibitors of the enzymes that may be useful as herbicides or herbicide synergists. This is desirable because the enzymes described herein catalyze the sulfhydryl conjugation of glutathione to compounds toxic to the plant. Conjugation can result in detoxification of these compounds. It is likely that inhibition of the detoxification process will result in inhibition of plant growth or plant death. Thus, the instant soybean GST enzymes could be appropriate for new herbicide or herbicide synergist discovery and design.

All or a portion of the nucleic acid fragments of the instant invention may also be used as probes for genetically and physically mapping the genes that they are a part of, and as markers for traits linked to expression of the instant enzymes. Such information may be useful in plant breeding in order to develop lines with desired phenotypes or in the identification of mutants.

For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., *Genomics* 1:174–181 (1987)) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al., (1980) *Am. J Hum. Genet.* 32:314–331).

The production and use of plant gene-derived probes for use in genetic mapping are described by Bernatzky, R. and Tanksley, S. D. (*Plant Mol. Biol. Reporter* 4(1):37–41 (1986)). Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al., In: *Nonmammalian Genomic Analysis: A Practical Guide*, Academic press, pp. 319–346 (1996), and references cited therein).

In another embodiment, nucleic acid probes derived from the instant nucleic acid sequences may be used in direct fluorescence in situ hybridization (FISH) mapping. Although current methods of FISH mapping favor use of large clones (several to several hundred KB), improvements in sensitivity may allow performance of FISH mapping using shorter probes.

A variety of nucleic acid amplification-based methods of genetic and physical mapping may be carried out using the instant nucleic acid sequences. Examples include allele-specific amplification, polymorphism of PCR-amplified fragments (CAPS), allele-specific ligation, nucleotide extension reactions, Radiation Hybrid Mapping and Happy Mapping. For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, this is generally not necessary for mapping methods. Such information may be useful in plant breeding in order to develop lines with desired starch phenotypes.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual;* Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Example 1

Composition of cDNA Libraries: Isolation and Sequencing of cDNA Clones cDNA libraries representing mRNAs from various soybean tissues were prepared. The characteristics of the libraries are described in Table 1.

TABLE 1 cDNA Libraries From Soybean Tissues

| Library | GST Class | Clone | Tissue |
|---|---|---|---|
| se1 | I | se1.27b04 | Soybean embryo |
| ssm | II | ssm.pk0026.g11 | soybean shoot meristem |
| NA | III | GSTa | NA |
| se3 | III | se3.03b09 | Soybean embryo |
| se6 | III | se6.pk0037.h4 | Soybean embryo |
| se6 | III | se6.pk0048.d7 | Soybean embryo |
| ses8w | III | ses8w.pk0028.c6 | mature embryo 8 weeks after subculture |
| sr1 | III | sr1.pk0011.d6 | Soybean root library |
| ssl | III | ssl.pk0002.f7 | soybean seedling 5–10 day |
| ssl | III | ssl.pk0005.e6 | soybean seedling 5–10 day |
| ssl | III | ssl.pk0014.a1 | soybean seedling 5–10 day |
| ssl | III | ssl.pk0020.b10 | soybean seedling 5–10 day |
| ssm | III | ssm.pk0067.g5 | soybean shoot meristem |
| se1 | IV | se1.pk0017.f5 | Soybean embryo |
| sfl1 | gst I | sfl1.pk126.i6 | Soybean (Glycine max L.) immature flower |
| sde4c | gst I | sde4c.pk002.d4 | Soybean (Glycine max L.) developing embryo (9–11 mm) |
| sdp2c | gst I | sdp2c.pk002.l16 | Soybean (Glycine max L.) developing pods 6–7 mm |
| sls1c | gst I | sls1c.pk003.f24 | Soybean (Glycine max L., S1990) infected with *Sclerotinia sclerotiorum mycelium* |
| sl2 | gst III | sl2.pk0010.e2 | Soybean (Glycine max L.) two week old developing seedlings treated with 2.5 ppm chlorimuron |
| sgs2c | gst III | sgs2c.pk001.n19 | Soybean (Glycine max L.) seeds 14 hrs after germination |
| sfl1 | gst III | sfl1.pk127.o7 | Soybean (Glycine max L.) immature flower |
| srr3c | gst III | srr3c.pk001.a17 | Soybean (Glycine max L., Bell) roots |
| sgs1c | gst III | sgs1c.pk001.c16 | Soybean (Glycine max L.) seeds 4 hrs after germination |
| sls2c | gst III | sls2c.pk002.d9 | Soybean (Glycine max L., Manta) infected with *Sclerotinia sclerotiorum mycelium* |

TABLE 1-continued cDNA Libraries From Soybean Tissues

| Library | GST Class | Clone | Tissue |
|---|---|---|---|
| sls1c | gst III | sls1c.pk007.j17 | Soybean (Glycine max L., S1990) infected with *Sclerotinia sclerotiorum* mycelium |
| src3c | gst III | src3c.pk026.e6 | Soybean (Glycine max L., Bell) 8 day old root inoculated with eggs of Cyst Nematode (Race14) for 4 days | cDNA Library Preparation

For clones other than GSTa, cDNA libraries were prepared in Uni-ZAP™ XR vectors according to the manufacturer's protocol (Stratagene Cloning Systems, La Jolla, Calif.). The Uni-ZAP™ XR libraries were converted into plasmid libraries according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences. Amplified insert DNAs were sequenced in dye-primer sequencing reactions to generate partial cDNA sequences (expressed sequence tags or "ESTs"; see Adams, M. D. et al., *Science* 252:1651 (1991)). The resulting ESTs were analyzed using a Perkin Elmer Model 377 fluorescent sequencer.

Cloning of GSTa

The GSTa clone was isolated and cloned using primers derived from a published GST sequence, GH2/4 (Flurry et al., *Physiologia Plantarum* 94 (1995) 594–604) according to the following protocol.

Soybeans (cv Williams 82) were germinated in vermiculite in a controlled growth room at 23° C. with 14-h light/10-h dark cycle at 330 $\mu E$ $m^{-2}$ $s^{-1}$. One week old seedlings were treated with 1 mM 2,4-D for 24 h before harvest. Seedlings were frozen in liquid nitrogen and ground with a mortar and pestle and RNA was prepared using TriZol reagent (Life Technologies Bethesda, Md.). Approximately 1.5 $\mu g$ of total RNA was reverse transcribed using the GeneAmp Kit (Perkin Elmer, Branchburg, N.J.) and oligo dT primer. The resulting first strand cDNA was used as a template for PCR amplification with AmpliTaq (Perldn Elmer) and the following primers: primer 1: (GAY GAR GAN CTN CTN GAY TTY TGG) (SEQ ID NO:29) and primer 2: (GAC TCG AGT CGA CAT GCT $T_{16}$) (SEQ ID NO:30). Primer 1 and primer 3 (see below) were designed based on N-terminal protein sequence previously described (Flury et al., 1995, supra). A Perlin-Elmer Thermal Cycle was allowed to cycle at 95° C. for 30 sec, 52° C. for 30 sec and 72° C. for 30 sec for 30 cycles. The resulting PCR product was cloned in pCR2.1 (Invitrogen, San Diego, Calif.) according to the manufacturer's instructions, named pBD16 and sequenced using an ABI sequencer. Primer 1 was designed to take advantage of the lack of degeneracy for encoding tryptophan. Because of this, the clone did not include the entire coding region and a second round of PCR was performed using the following primers: Primer 3: CAT ATG AGT GAT GAG GTA GTG TTA TTA GAT TTC TGG (SEQ ID NO:31) and Primer 4: TTA TTA CAC AAA TAT TAC TTA TTT GAA AGG CTA A (SEQ ID NO:32) and using 0.002 $\mu g$ of linearized pBD16 as a template. Again, the resulting PCR product was cloned into pCR2.1 and named pBD17 and sequenced using an ABI sequencer. Additional gene specific primers were made and used to determine the complete sequence. All regions were sequenced at least two times in both directions. The nucleotide sequence and encoded protein sequence are shown in SEQ ID NO:5 and SEQ ID NO:6, respectively.

Example 2

Identification and Charactenzation of cDNA Clones cDNAs encoding soybean GST enzymes were identified by conducting BLAST (Basic Local Alignment Search Tool; Altschul, S. F., et al., (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the eDNA sequence and the BLAST "hit" represent homologous proteins.

All comparisons were done using either the BLASTNnr or BLASTXnr algorithm. The results of the BLAST comparison is given in Table 2 which summarize the clones and the sequences to which they have the most similarity. Table 2 displays data based on the BLASTNnr or BLASTXnr algorithm with values reported in pLogs or expect values. The Expect value estimates the statistical significance of the match, specifying the number of matches, with a given score, that are expected in a search of a database of this size absolutely by chance.

Each cDNA identified encodes at least a portion of either a GST Class I, II, III, or IV.

Example 5 describes the strategy for sequencing the above described clones.

TABLE 2

BLAST Results For Clones

| Clone | GST Class | Similarity Identified | SEQ ID NO. Base | SEQ ID NO. Peptide | Blast Algorithm | pLog Score*/E-Value** | Citation |
|---|---|---|---|---|---|---|---|
| se1.27b04 | I | X06754\|ZMGST1 Maize mRNA for GSH gluthathione S-transferase I | 1 | 2 | Nnr | 41.35 | |
| ssm.pk0026.g11 | II | \|X58390\|DCCARSR8 *D. caryophyllus* CARSR8 mRNA for glutathione s-transferase | 3 | 4 | Nnr | 85.02 | |
| GSTa | III | Y10820\|GMGLUTTR *G. max* mRNA for glutathione transferase | 5 | 6 | Nnr | 257.95 | |
| se3.03b09 | III | M20363\|SOYHSP Soybean heat-shock protein (Gmhsp26-A) gene | 7 | 8 | Nnr | 28.72 | |
| se6.pk0037.h4 | III | M20363\|SOYHSP Soybean heat-shock protein (Gmhsp26-A) gene, complete cds | 9 | 10 | Nnr | 247.44 | |
| se6.pk0048.d7 | III | Y10820\|GMGLUTTR *G.max* mRNA for glutathione transferase | 11 | 12 | Nnr | 0.0 | |
| ses8w.pk0028.c6 | III | M20363\|SOYHSP Soybean heat-shock protein (Gmhsp26-A) gene, complete cds. | 13 | 14 | Nnr | 269.17 | |
| sr1.pk0011.d6 | III | U20809\|VRU20809 *Vigna radiata* clone MII-4 auxin-induced protein mRNA, partial cds | 15 | 16 | Nnr | 229.82 | |
| ssl.pk0002.f7 | III | X68819\|GMGLYO *G.max* mRNA for Glyoxalase I | 17 | 18 | Nnr | 206.01 | |
| ssl.pk0005.e6 | III | Y10820\|GMGLUTTR *G.max* mRNA for glutathione transferase | 19 | 20 | Xnr | 296.05 | |
| ssl.pk0014.a1 | III | M20363\|SOYHSP Soybean heat-shock protein (Gmhsp26-A) gene, complete cds | 21 | 22 | Nnr | 166.96 | |
| ssl.pk0020.b10 | III | M20363\|SOYHSP Soybean heat-shock protein (Gmhsp26-A) gene, complete cds. | 23 | 24 | Nnr | 34.76 | |
| ssm.pk0067.g5 | III | M20363\|SOYHSP Soybean heat-shock protein (Gmhsp26-A) gene, complete cds | 25 | 26 | Nnr | 104.00 | |
| se1.pk0017.f5 | IV | \|X58573\|ZMIN21 Maize In2-1 mRNA | 27 | 28 | Nnr | 72.04 | |
| src3c.pk026.e6 | gst III | Q03662\|GTX1__Tobac Probable Glutathione S-Transferase (Auxin-Induced Protein Pgnt1/Pcnt110) | 33 | 34 | Xnr | 4e-50 | van der Zaal et al., Plant Mol. Biol. 16(6), 983–998 (1991) |
| sls1c.pk007.j17 | gst III | P32110\|GTX6__Soybn Probable Glutathione S-Transferase (Heat Shock Protein 26A) | 35 | 36 | Xnr | 1e-53 | Czarnecka et al., Mol. Cell. Biol. 8(3), 1113–1122 (1988) |
| sls2c.pk002.d9 | gst III | P77526\|YFCG__Ecoli Hypothetical 24.5 Kd Protein In Pta-Folx Intergenic Region >gi\|1788640 (AE000319) putative S-transferase [*Escherichia coli*] | 37 | 38 | Xnr | 2e-38 | Blattner et al., Science 277 (5331), 1453–1474 (1997) |
| sls1c.pk003.f24 | gst I | (U43126) glutathione S-transferase III homolog [*Naegleria fowleri*] | 39 | 40 | Xnr | 3e-55 | Shaw et al., Unpublished |
| sdp2c.pk002.l16 | gst I | (AC004669) glutathione S-transferase [*Arabidopsis thaliana*] | 41 | 42 | Xnr | 8e-69 | Rounsley et al., Unpublished |

TABLE 2-continued

BLAST Results For Clones

| Clone | GST Class | Similarity Identified | SEQ ID NO. Base | SEQ ID NO. Peptide | Blast Algorithm | pLog Score*/E-Value** | Citation |
|---|---|---|---|---|---|---|---|
| sfl1.pk127.o7 | gst III | (AF048978) 2,4-D inducible glutathione S-transferase [Glycine max] | 43 | 44 | Xnr | 1e-81 | McGonigle et al., Plant Physiol. 117, 332 (1998) |
| sfl1.pk126.i6 | gst I | (AC004669) glutathione S-transferase [Arabidopsis thaliana] | 45 | 46 | Xnr | 2e-78 | Rounsley et al., Unpublished |
| srr3c.pk001.a17 | gst III | P32110\|GTX6_Soybn Probable Glutathione S-Transferase (Heat Shock Protein 26A) | 47 | 48 | Xnr | 4e-48 | Czarnecka et al., Mol. Cell. Biol. 8(3), 1113–1122 (1988) |
| sgs1c.pk001.c16 | gst III | Q03664\|GTX3_Tobac Probable Glutathione S-Transferase (Auxin-Induced Protein Pcnt103) | 49 | 50 | Xnr | 3e-52 | van der Zaal et al., Plant Mol. Biol. 16(6), 983–998 (1991) |
| sl2.pk0010.e2 | gst III | P32110\|GTX6_Soybn Probable Glutathione S-Transferase (Heat Shock Protein 26A) | 51 | 52 | Xnr | 6e-51 | Czarnecka et al., Mol. Cell. Biol. 8(3), 1113–1122 (1988) |
| sgs2c.pk001.n19 | gst III | Q03663\|GTX2_Tobac Probable Glutathione S-Transferase (Auxin-Induced Protein Pgnt35/Pcnt111) | 53 | 54 | Xnr | 6e-51 | van der Zaal et al., Plant Mol. Biol. 16(6), 983–998 (1991) |
| sde4c.pk002.d4 | gst I | (AJ131580) glutathione transferase AtGST 10 [Arabidopsis thaliana] | 55 | 56 | Xnr | 8e-96 | Dixon et al., Unpublished |

*Plog represents the negative of the logarithm of the reported P-value
**Expect value. The Expect value estimates the statistical significance of the match, specifying the number of matches, with a given score, that are expected in a search of a database of this size absolutely by chance Example 3

Expression of Chimeric Genes Encoding Soybean GST Enzymes in Maize Cells (Monocotyledon)

A chimeric gene comprising a cDNA encoding a soybean GST enzyme in sense orientation can be constructed by polymerase chain reaction (PCR) of the eDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a 100 µL volume in a standard PCR mix consisting of 0.4 mM of each oligonucleotide and 0.3 pM of target DNA in 10 mM Tris-HCl, pH 8.3, 50 mM KCl, 1.5 mM MgCl$_2$, 200 mM dGTP, 200 mM dATP, 200 mM dTTP, 200 mM dCTP and 0.025 unit DNA polymerase. Reactions are carried out in a Perkin-Elmer Cetus Thermocycler™ for 30 cycles comprising 1 min at 95° C., 2 min at 55° C. and 3 min at 72° C., with a final 7 min extension at 72° C. after the last cycle. The amplified DNA is then digested with restriction enzymes NcoI and SmaI and fractionated on a 0.7% low melting point agarose gel in 40 mM Tris-acetate, pH 8.5, 1 mM EDTA. The appropriate band can be excised from the gel, melted at 68° C. and combined with a 4.9 kb NcoI-SmaI fragment of the plasmid pML103. Plasmid pML103 has been deposited under the terms of the Budapest Treaty with the ATCC and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega Corp., 7113 Benhart Dr., Raleigh, N.C.). Vector and insert DNA can be ligated at 15° C. overnight, essentially as described (Maniatis). The ligated DNA may then be used to transform E. coli XL1-Blue (Epicurian Coli XL-1; Stratagene). Bacterial transformants can be screened by restriction enzyme digestion of plasmid DNA and limited nucleotide sequence analysis using the dideoxy chain termination method (DNA Sequencing Kit, U.S. Biochemical). The resulting plasmid construct would comprise a chimeric gene encoding, in the 5' to 3' direction, the maize 27 kD zein promoter, a cDNA fragment encoding a plant gst enzyme, and the 10 kD zein 3' region.

The chimeric gene so constructed can then be introduced into corn cells by the following procedure. Immature corn embryos can be dissected from developing caryopses derived from crosses of the inbred corn lines H99 and LH132 (Indiana Agric. Exp. Station, Indiana, USA). The embryos are isolated 10 to 11 days after pollination when they are 1.0 to 1.5 mm long. The embryos are then placed with the axis-side facing down and in contact with agarose-solidified N6 medium (Chu et al., Sci Sin. Peking 18:659–668 (1975)). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks. The plasmid, p35S/Ac (obtained from Dr. Peter Eckes, Hoechst Ag, v Frankfurt, Germany), may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. *Nature* 313:810–812 (1985)) and the 3M region of the nopaline synthase gene from the T-DNA of the Ti plasmid of *Agrobacterium tumefaciens*. The particle bombardment method (Klein et al., *Nature* 327:70–73 (1987)) may be used to transfer genes to the callus culture cells. According to this method, gold particles (1 μm in diameter) are coated with DNA using the following technique. Ten ug of plasmid DNAs are added to 50 μL of a suspension of gold particles (60 mg per mL). Calcium chloride (50 uL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a flying disc (Bio-Rad Labs, 861 Ridgeview Dr, Medina, Ohio). The particles are then accelerated into the corn tissue with a PDS-1000/He (Bio-Rad Labs, 861 Ridgeview Dr., Medina, Ohio), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covers a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks, the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium. Plants can be regenerated from the transgenic callus by first transferring clusters of tissue to N6 medium supplemented with 0.2 mg per liter of 2,4-D. After two weeks, the tissue can be transferred to regeneration medium (Fromm et al., *Bio/Technology* 8:833–839 (1990)).

Example 4

Exression of Chimeric Genes in Tobacco Cells (Dicotyledon)

Cloning sites (XbaI or SmaI) can be incorporated into the oligonucleotides to provide proper orientation of the DNA fragment when inserted into the digested vector pBI121 (Clonetech Inc., 6500 Donlon Rd, Somis, Calif.) or other appropriate transformation vector. Amplification could be performed as described above and the amplified DNA would then be digested with restriction enzymes XbaI and SmaI and fractionated on a 0.7% low melting point agarose gel in 40 mM Tris-acetate, pH 8.5, 1 mM EDTA. The appropriate band can be excised from the gel, melted at 68° C. and combined with a 13 kb XbaI-SmaI fragment of the plasmid pBI121 and handled as in Example 3. The resulting plasmid construct would comprise a chimeric gene encoding, in the 5' to 3' direction, right border region, the nos promoter linked to the NPT II gene and a nos terminator region followed by a cauliflower mosaic virus 35S promoter linked to a cDNA fragment encoding a plant GST enzyme and the nos terminator 3' region flanked by the left border region. The resulting plasmid could be mobilized into the Agrobacterium strain LBA4404/pAL4404 (Hoekema et al. *Nature* 303:179–180, (1983) using tri-parental matings (Ruvkin and Ausubel, *Nature* 289:85–88, (1981)). The resulting Agrobacterium strains could be then cocultivated with protoplasts (van den Elzen et al. *Plant Mol. Biol,* 5:149–154 (1985)) or leaf disks (Horsch et al. *Science* 227:1229–1231, (1985)) of *Nicotiana tabacum* cv Wisconsin 38 and kanarnycin-resistant transformants would be selected. Kanamycin-resistant transformed tobacco plants would be regenerated.

Example 5

Expression Of Chimeric Genes In Microbial Cells And Purification of Gene Product Example 5 illustrates the expression of isolated full length genes encoding class I, II, III or IV GST proteins in *E. coli*.

All clones listed in Tables 2 were selected on the basis of homology to known GSTs using the BLAST algorithm as described in Example 2. Plasmid DNA was purified using QLAFilter cartridges (Qiagen. Inc., 9600 De Soto Ave, Chatsworth, Calif.) according to the manufacturer's instructions. Sequence was generated on an ABI Automatic sequencer using dye terminator technology (U.S. Pat. No. 5,366,860; EP 272007) using a combination of vector and insert-specific primers. Sequence editing was performed in either DNAStar (DNA, Star Inc.) or the Wisconsin GCG program (Wisconsin Package Version 9.0, Genetics Computer Group (GCG), Madison, Wis.). All sequences represent coverage at least two times in both directions.

cDNA from full length clones listed in Table 2 encoding the instant soybean GST enzymes were inserted into the ligation independent cloning (LIC) pET30 vector (Novagen, Inc., 597 Science Dr, Madison, Wis.) under the control of the T7 promoter, according to the manufacturer's instructions (see Novagen publications "LIC Vector Kits", publication number TB163 and U.S. Pat. No. 4,952,496). The vector was then used to transform BL21(DE3) competent *E. coli* hosts. Primers with a specific 3' extension designed for ligation independent cloning were designed to amplify the GST gene (Maniatis). Amplification products were gel-purified and annealed into the LIC vector after treatment with T4 DNA polymerase (Novagen). Insert-containing vectors were then used to transform NovaBlue competent *E. coli* cells and tansformants were screened for the presence of viable inserts. Clones in the correct orientation with respect to the T7 promoter were transformed into BL21(DE3) competent cells (Novagen) and selected on LB agar plates containing 50 μg/mL kanamycin. Colonies arising from this transformation were grown overnight at 37° C. in Lauria Broth to OD 600=0.6 and induced with 1 mM IPTG and allowed to grow for an additional two hours. The culture was harvested, resuspended in binding buffer, lysed with a French press and cleared by centrifugation.

Expressed protein was purified using the HIS binding kit (Novagen) according to the manufacturer's instructions. Purified protein was examined on 15–20% SDS Phast Gels (Bio-Rad Laboratories, 861 Ridgeview Dr, Medina, Ohio) and quantitated spectrophotometrically using BSA as a standard. Protein data is tabulated below in Table 3.

TABLE 3

Protein Expression Data

| CLONE | OD. 280 |
|---|---|
| se1.27b04 | 0.5 |
| ssm.pk0026.g11 | 0.44 |
| GSTa | 53.6 |
| se3.03b09 | 29.1 |
| se6.pk0037.h4 | 0.6 |
| se6.pk0048.d7 | 1.41 |
| ses8w.pk0028.c6 | 0.56 |
| sr1.pk0011.d6 | 0.55 |
| ss1.pk0002.f7 | 0.70 |
| ss1.pk0005.e6 | 0.51 |
| ss1.pk0014.a1 | 0.62 |
| ss1.pk0020.b10 | 1.14 |
| ssm.pk0067.g5 | 1.64 |
| se1.pk0017.f5 | 0.37 |

Example 6

Screening Of Expressed GST Enzymes For Substrate Metabolism

The GST enzymes, expressed and purified as described in Example 5 were screened for their ability to metabolize a variety of substrates. Substrates tested included the three herbicide electrophilic substrates chlorimuron ethyl, alachlor, and Atrazine, and four model electrophilic substrates, 1-chloro-2, 4-dinitro-benzene (CDNB), ethacrynic acid, t-stilbene oxide, and 1,2-epoxy-3-(p-nitrophenoxy) propane. The enzymes were purified as described in Example 5 and used in the following assay.

For each enzyme, the conjugation reaction with each electrophilic substrate was performed by incubating 0.3 to 30 μg enzyme in 0.1 M MOPS (pH 7.0) containing 0.4 mM of the electrophilic substrate. The reaction was inititated by the addition of glutathione to a final concentration of 4 mM. After 5 to 30 min, the reaction was terminated by the addition of 45 μL acetonitrile, microfuged for 10 min to remove precipitated protein, and then the supernatent was removed and added to 65 μL of water. This sample was chromatographed on a Zorbax C8 reverse phase HPLC column (3 μm particle size, 6.2 mm×8 cm) using a combination of linear gradients (flow=1.5 mL/min) of 1% $H_3PO_4$ in water (solvent A) and 1% $H_3PO_4$ in acetonitile. The gradient started with 5% solvent B, progressing from 5% to 75% solvent B between 1 and 10 min, and from 75% to 95% solvent B between 10 and 12 min. Control reactions without enzyme were performed to correct for uncatalyzed reaction. Quantitation of metabolites were based on an assumption that the extinction coefficient of the conjugate was identical to that of the electrophilic substrate.

Table 4 shows the activity of each enzyme measured in $nmol.min^{-1}.mg^{-1}$ with the seven different substrates. Activities are related to the activity of a known and previously isolated and purified GST enzyme, GH2/4 (also called GST 26) (Czarnecka et al., *Plant Molecular Biology* 3:45–58 (1984); Ulmasoz et al., *Plant Physiol* 108:919–927 (1995)).

TABLE 4

Activities of Soybean GST Enzymes

| GST Name | GST Class | Chlorimuron Ethyl | Alachlor | Atrazine | CDNB | Ethacrynic Acid | T-Stilbene Oxide | 1,2-epoxy-3-(p-nitrophenoxy)propane |
|---|---|---|---|---|---|---|---|---|
| se6.pk0037.h4 | III | 0.1 | 1 | 0.19 | 2364 | 13 | 0.06 | 1 |
| GH2/4 | III | 0.5 | 104 | 0.13 | 6030 | 8 | 7.93 | 33 |
| ses8w.pk0028.c6 | III | 0.2 | 10 | 1.40 | 515 | 17 | 4.04 | 12 |
| sr1.pk0034.c5 | III | 0.3 | 111 | 0.46 | 2545 | 14 | 0.12 | 10 |
| se6.pk0044.b7 | III | 0.1 | 0 | 0.00 | 45 | 9 | 0.00 | 1 |
| ssm.pk0067.g5 | III | 0.1 | 4 | 0.03 | 1394 | 13 | 0.49 | 19 |
| ssl.pk0020.b10 | III | 0.1 | 7 | 0.03 | 470 | 14 | 0.02 | 47 |
| GST-A | III | 0.5 | 71 | 0.03 | 1924 | 109 | 0.06 | 22 |
| ssl.pk0005.e6 | III | 1.4 | 166 | 0.00 | 2030 | 11 | 0.06 | 4 |
| se6.pk0048.d7 | III | 0.5 | 8 | 0.76 | 1379 | 4 | 0.07 | 9 |
| ssl.pk0002.f7 | III | 0.9 | 30 | 0.00 | 2576 | 68 | 0.16 | 10 |
| se3.03b09 | III | 4.4 | 168 | — | 14364 | 1 | 0.07 | 20 |
| se1.27b04 | I | 0.1 | 0 | 0.00 | 15 | 11 | 0.00 | 0 |
| ssm.pk0026.g11 | II | 0.0 | 0 | 0.00 | 15 | 5 | 0.04 | 2 |
| se1.pk0017.f5 | IV | 0.0 | 0 | 0.00 | 30 | 3 | 0.15 | 0 |

What is claimed is:

1. An isolated nucleic acid encoding a soybean glutathione S-transferase (GST) enzyme selected from the group consisting of:
   (a) an isolated nucleic acid encoding the amino acid sequence selected from the group consisting of SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, and SEQ ID NO:56;
   (b) an isolated nucleic acid that is 90% identical to the nucleic acid of (a); and
   (c) an isolated nucleic acid that is complementary to the nucleic acid of (a) or (b).

2. The isolated nucleic acid of claim 1 selected from the group consisting of SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, and SEQ ID NO:55.

3. A chimeric gene comprising the isolated nucleic acid of claim 1 operably linked to a suitable regulatory sequence.

4. A transformed host cell comprising a host cell and the chimeric gene of claim 3.

5. The transformed host cell of claim 4 wherein the host cell is a plant cell.

6. The transformed host cell of claim 4 wherein the host cell is of the species E. coli.

7. A method of altering the level of expression of a soybean GST enzyme in a host cell comprising:
   (a) transforming a host cell with the chimeric gene of claim 3 and;
   (b) growing the transformed host cell produced in step (a) under conditions that are suitable for expression of the chimeric gene resulting in production of altered levels of a soybean GST enzyme in the transformed host cell relative to expression levels of an untransformed host cell.

8. A method of obtaining a nucleic acid encoding a soybean GST enzyme comprising:
   (a) probing a cDNA or genomic library with a nucleic acid fragment of the nucleic acid of claim 1;
   (b) identifying a DNA clone that hybridizes with said nucleic acid fragment; and
   (c) sequencing said DNA clone,
wherein said clone encodes a soybean GST enzyme.

9. A method of obtaining a nucleic acid encoding a soybean GST enzyme comprising:
   (a) synthesizing at least one oligonucleotide primer corresponding to a portion of the sequence of claim 1; and
   (b) amplifying a cDNA insert present in a cloning vector using the said oligonucleotide primer,
wherein said cDNA insert encodes a soybean GST enzyme.

10. A method for identifying a chemical compound that inhibits the activity of a soybean GST enzyme encoded by the nucleic acid of claim 1, the method comprising the steps of:
   (a) transforming a host cell with a chimeric gene comprising the nucleic acid of claim 1 encoding a soybean GST enzyme, the chimeric gene operably linked to at least one suitable regulatory sequence;
   (b) growing the transformed host cell of step (a) under conditions suitable for expression of the chimeric gene resulting in production of the GST enzyme;
   (c) optionally purifying the GST enzyme expressed by the transformed host cell;
   (d) contacting the GST enzyme with a chemical compound of interest; and
   (e) identifying the chemical compound of interest that reduces the activity of the soybean GST enzyme relative to the activity of the soybean GST enzyme in the absence of the chemical compound of interest.

11. The method of claim 10 wherein step (d) is carried out in the presence of at least one electrophilic substrate and at least one thiol donor selected from the group consisting of glutathione and homoglutathione.

12. The method of claim 10 wherein the nucleic acid is selected from the group consisting of SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, and SEQ ID NO:55, and wherein the GST enzyme is selected from the group consisting of SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, and SEQ ID NO:56.

13. A method for identifying a substrate for a GST enzyme, the GST enzyme encoded by the isolated nucleic acid of claim 1, the method comprising the steps of:
   (a) transforming a host cell with a chimeric gene comprising an isolated nucleic acid of claim 1 encoding a soybean GST enzyme, the chimeric gene operably linked to at least one suitable regulatory sequence;
   (b) growing the transformed host cell of step (a) under conditions suitable for expression of the chimeric gene resulting in production of the soybean GST enzyme;
   (c) optionally purifying the GST enzyme expressed by the transformed host cell;
   (d) contacting the soybean GST enzyme with a substrate candidate; and
   (e) identifying a substrate for a GST enzyme that increases the activity of the soybean GST enzyme relative to the activity of the soybean GST enzyme in the absence of the substrate.

14. The method of claim 13 wherein step (d) is carried out in the presence of at least one thiol donor selected from the group consisting of glutathione and homoglutathione.

15. The method of claim 13 wherein the nucleic acid of claim 1 is selected from the group consisting of SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, and SEQ ID NO:55, and wherein the soybean GST enzyme is selected from the group consisting of SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, and SEQ ID NO:56.

* * * * *